United States Patent
Damelin et al.

(10) Patent No.: US 9,340,774 B2
(45) Date of Patent: May 17, 2016

(54) TUMOR-INITIATING CELLS AND METHODS FOR USING SAME

(75) Inventors: Marc Isaac Damelin, Park Ridge, NJ (US); Kenneth G. Geles, Peirmont, NY (US); Jonathon P. Golas, Hewitt, NJ (US); Erwin Boghaert, Pleasant Prairie, WI (US); Bin-Bing S. Zhou, Ho-Ho-Kus, NJ (US)

(73) Assignee: Wyeth LLC, Madison, NJ (US)

( * ) Notice: Subject to any disclaimer, the term of this patent is extended or adjusted under 35 U.S.C. 154(b) by 273 days.

(21) Appl. No.: 13/260,459

(22) PCT Filed: Mar. 26, 2010

(86) PCT No.: PCT/US2010/028926
§ 371 (c)(1),
(2), (4) Date: Dec. 7, 2011

(87) PCT Pub. No.: WO2010/111659
PCT Pub. Date: Sep. 30, 2010

(65) Prior Publication Data
US 2012/0071350 A1 Mar. 22, 2012

Related U.S. Application Data

(60) Provisional application No. 61/164,272, filed on Mar. 27, 2009.

(51) Int. Cl.
*C12N 5/095* (2010.01)
*G01N 33/574* (2006.01)

(52) U.S. Cl.
CPC ........ *C12N 5/0695* (2013.01); *C12N 2501/385* (2013.01); *C12N 2501/60* (2013.01)

(58) Field of Classification Search
None
See application file for complete search history.

(56) References Cited

U.S. PATENT DOCUMENTS

| | | | |
|---|---|---|---|
| 5,869,053 | A | 2/1999 | Stern et al. |
| 5,942,225 | A | 8/1999 | Bruder et al. |
| 2006/0088522 | A1 | 4/2006 | Boghaert et al. |
| 2007/0010469 | A1* | 1/2007 | Chan et al. ............. 514/44 |
| 2007/0231333 | A1 | 10/2007 | Boghaert et al. |

FOREIGN PATENT DOCUMENTS

| | | | |
|---|---|---|---|
| WO | WO 89/07947 | 9/1989 | |
| WO | WO 2004/005926 | 1/2004 | |
| WO | WO2006/031653 | * 3/2006 | ............. A61K 47/48 |
| WO | WO 2006/031653 | 5/2006 | |
| WO | WO 2007/053648 | 5/2007 | |
| WO | WO 2007/106744 | 9/2007 | |

OTHER PUBLICATIONS

"TroVax Oxford BioMedica clinical data (phase II) (colorectal cancer)" published Mar. 14, 2005 (R& D Focus Drug News) (hereafter called "The TroVax 2005 reference").*
"naptumomab estafenatox Active Biotech Orphan Drug, EU(renal cancer) Active Biotech phase change III, Europe(renal cancer)" published Aug. 6, 2007 (R & D Focus Drug News) (hereafter called "The naptumomab estafenatox 2007 reference").*
"Active Biotech Presents Survival Data on Cancer Drug" (PrimeZone Media Network published Sep. 29, 2005; Abstract only.*
"American Society of Clinical Oncology Positive Sorafenib Data Lead to Analyst Downgrade, Stock Drop" (Bioworld Today published May 17, 2005; pp. 1-5).*
Al-Hajj et al., "Prospective identification of tumorigenic breast cancer cells", *Proc. Natl. Acad. Sci. USA*, 2003, 100: 3983-3988.
Ali et al., "The pattern of expression of the 5T4 oncofoetal antigen on normal, dysplastic and malignant oral mucosa," *Oral Oncology*, 2001, 37: 57-64.
Avilion et al., "Multipotent cell lineages in early mouse development depend on SOX2 function," *Genes & Dev.*, 2003, 17: 126-140.
Bao et al., "Cancer stem cells promote radioresistance of malignant glioma through preferential activation of DNA damage checkpoint and repair," *Nature*, 2006, 444: 756-760.
Bao et al., "Targeting cancer stem cells through L1CAM suppresses glioma growth," *Cancer Res.*, 2008, 68: (15) 6043-6048.
Bonnet et al "Human acute myeloid leukemia is organized as a hierarchy that originates from a primitive hematopoietic cell," *Nat. Med.*, 1997, 3(7): 730-737.
Boyer et al., "Core transcriptional regulatory circuitry in human embryonic stem cells," *Cell*, 2005, 122: 947-956.
Connor et al, "Loss of MHC class-I expression in cervical carcinomas.," *Int. J. Cancer*, 1990, 46(6): 1029-1034.
Dalerba et al., "Phenotypic characterization of human colorectal cancer stem cells.," Proc. Natl. Acad. Sci. USA, 2007, 104: 10158-10163.
Dang et al., "Chromosome 19 translocation, overexpression of Notch3, and human lung cancer," *J. Natl. Cancer Inst.*, 2000, 92, 1355-1357.
Donnenberg, V. et al "Tumorigenic stem and progenitor cells: Implications for the therapeutic index of anti-cancer agents" *J. Control Release*, 2007, 122(3): 385-391.
Eramo et al., "Identification and expansion of the tumorigenic lung cancer stem cell population," *Cell Death Differ.*, 2008, 15: 504-514.
Filmore , et al "Human breast cancer cell lines contain stem-like cells that self-renew, give rise to phenotypically diverse progeny and survive chemotherapy.," *Breast Cancer Res.*, 2008, 10: R25, 1-13.
Glinsky et al., "Microarray analysis identifies a death-from-cancer signature predicting therapy failure in patients with multiple types of cancer," *J.Clin. Invest.*, 2005, 115(6): 1503-1521.
Godar et al., "Growth-inhibitory and tumor-suppressive functions of p53 depend on its repression of CD44 expression.," *Cell*, 2008, 134: 62-73.

(Continued)

*Primary Examiner* — Catherine S Hibbert
(74) *Attorney, Agent, or Firm* — Womble Carlyle Sandridge & Rice, LLP

(57) ABSTRACT

Isolated and enriched tumor-initiating cell populations, methods for preparing the same, and uses thereof.

11 Claims, 19 Drawing Sheets

(56) References Cited

OTHER PUBLICATIONS

Hermann et al., "Distinct populations of cancer stem cells determine tumor growth and metastatic activity in human pancreatic cancer," *Cell Stem Cell*, 2007, 1: 313-323.

Hole, "A 72 kD trophoblast glycoprotein defined by a monoclonal antibody," *Br. J. Cancer*, 1988, 57(3): 239-46.

Hole et al., "Isolation and characterization of 5T4, a tumour-associated antigen," *Int. J. Cancer*, 1990, 45: 179-84.

Jiang et al "Aldehyde dehydrogenase 1 is a tumor stem cell-associated marker in lung cancer." *Mol Cancer Res.*, Mar. 2009; 7(3):330-8.

Jones et al., "Investigation of expression of 5T4 antigen in cervical cancer," *Br. J. Cancer*, 1990, 61: 96-100.

Kitamura et al "Cancer stem cell: implications in cancer biology and therapy with special reference to lung cancer." *Lung Cancer*, 2009, 66(3):275-81.

Komagata et al, *Gan To Kagaku Ryoho*, 2004, 31(10): 1609-1613—Abstract Only.

Kondo et al., "Persistence of a small subpopulation of cancer stem-like cells in the C6 glioma cell line," *Proc. Natl. Acad. Sci. U.S.A.*, 2004, 101(3): 781-786.

Kuemmel et al., "TA-MUC1 epitope in non-small cell lung cancer," *Lung Cancer*, 2009, 63(1): 98-105.

Lee, J., et al., "Tumor stem cells derived from glioblastomas cultured in bFGF and EGF more closely mirror the phenotype and genotype of primary tumors than do serum-cultured cell lines.," *Cancer Cell*, 2006, 9: 391-403.

Li, C., et al., "Identification of pancreatic cancer stem cells," *Cancer Res.*, 2007, 67: 1030-1037.

Lobo et al., "The biology of cancer stem cells," Annu. Rev. Cell Dev. Biol., 2007 23: 675-699.

Loo et al "Antibody-based identification of cell surface antigens: targets for cancer therapy." *Curr Opin Pharmacol*, 2008, 8(5):627-31.

Marhaba et al "CD44 in cancer progression: adhesion, migration and growth regulation," *J. Mol. Histol.*, 2004, 35(3): 211-231.

Matsui et al., "Characterization of clonogenic multiple myeloma cells," *Blood*, 2004, 103: 2332-2336.

W. Mieke C. Mulder et al., "Low Intercellular Adhesion Molecule 1 and High 5T4 Expression on Tumor Cells Correlate with Reduced Disease-free Survival in Colorectal Carcinoma Patients," *Clin. Cancer Res.*, 1997, 3: 1923-1930.

Molina et al., "Mucins CA 125, CA 19.9, CA 15.3 and TAG-72.3 as tumor markers in patients with lung cancer: comparison with CYFRA 21-1, CEA, SCC and NSE," *Tumour Biol.*, 2008, 29(6): 371-380.

Naganuma, H., et al., "Oncofetal antigen 5T4 expression as a prognostic factor in patients with gastric cancer," *Anticancer Res.*, 2002, 22: 1033-1038.

O'Brien et al., "A human colon cancer cell capable of initiating tumour growth in immunodeficient mice," *Nature*, 2007, 445: 106-110.

Patrawala et al., "Side population is enriched in tumorigenic, stem-like cancer cells, whereas ABCG2+ and ABCG2– cancer cells are similarly tumorigenic," *Cancer Res.*, 2005, 65(14): 6207-6219.

Potten et al., "Stem cells: attributes, cycles, spirals, pitfalls and uncertainties. Lessons for and from the crypt," *Development*, 1990, 110: 1001-1020.

Prince, ME, et al., "Identification of a subpopulation of cells with cancer stem cell properties in head and neck squamous cell carcinoma," *Proc. Natl. Acad. Sci. USA*, 2007, 104: 973-978.

Reya et al, "Stem cells, cancer, and cancer stem cells," *Nature*, 2001, 414: 105-111.

Ricci-Vitiani et al., "Identification and expansion of human colon-cancer-initiating cells," *Nature*, 2007, 445: 111-115.

Schatton et al., "Identification of cells initiating human melanomas," *Nature*, 2008, 451: 345-349.

Slack, "Stem cells in epithelial tissues," *Science*, 2000, 287: 1431-1433.

Southall et al., "Immunohistological distribution of 5T4 antigen in normal and malignant tissues," *Br. J. Cancer*, 1990, 61:89-95.

Starzynska et al., "5T4 oncofetal antigen in gastric carcinoma and its clinical significance," Eur. J. Gastroenterol. Hepatol., 1998, 10: 479-484.

Starzynska et al., "The expression of 5T4 antigen in colorectal and gastric carcinoma," *Br. J. Cancer*, 1992, 66: 867-869.

Starzynska, T., et al "Prognostic significance of 5T4 oncofetal antigen expression in colorectal carcinoma" *Br. J. Cancer*, 1994, 69: 899-902.

Takahashi, K. et al, "Induction of pluripotent stem cells from mouse embryonic and adult fibroblast cultures by defined factors," *Cell*, 2006, 126: 663-676.

Ucar, D., et al; "Aldehyde dehydrogenase activity as a functional marker for lung cancer." *Chem Biol Interact*. Mar. 16, 2009: 178(1-3):48-55.

Visvader et al, "Cancer stem cells in solid tumours: accumulating evidence and unresolved questions," *Nat. Rev. Cancer*, 2008, 8: 755-768.

Wrigley et al., "5T4 oncofetal antigen expression in ovarian carcinoma," *Int. J. Gynecol. Cancer*, 1995, 5: 269-274.

Yu, F., et al., "let-7 regulates self renewal and tumorigenicity of breast cancer cells," *Cell*, 2007, 131: 1109-1123.

Levina et al "Drug-Selected Human Lung Cancer Stem Cells: Cytokine Network, Tumorigenic and Metastatic Properties", *PloS One*, Aug. 2008, 3(8), e3077 pp. 1-16.

Yu et al., "*let*-7 Regulates Self Renewal and Tumorigenicity of Breast Cancer Cells", *Cell*, 2007; 131:1109-1123.

Li et al., "Intrinsic Resistance of Tumorigenic Breast Cancer", *J Natl Cancer Inst*, 2008; 100:672-679.

\* cited by examiner

| Implant Line | Number of Tumors From: | |
|---|---|---|
| | 5T4[high] | 5T4[-/low] |
| 37622#1 | 6/10 | 1/10 |
| 37622#2 | 12/20 | 2/20 |
| 60257#1 | 6/10 | 2/10 |
| 60257#2 | 12/20 | 4/20 |

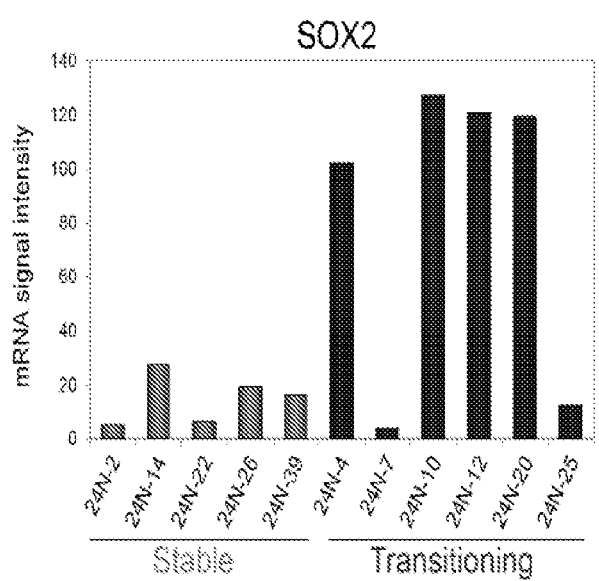
FIG. 9A
FIG. 9B
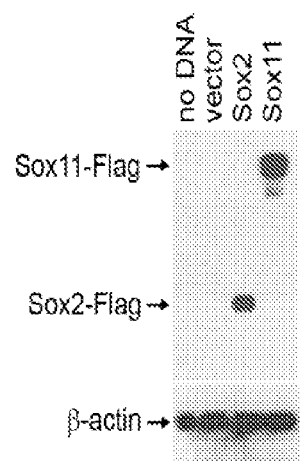
FIG. 9C
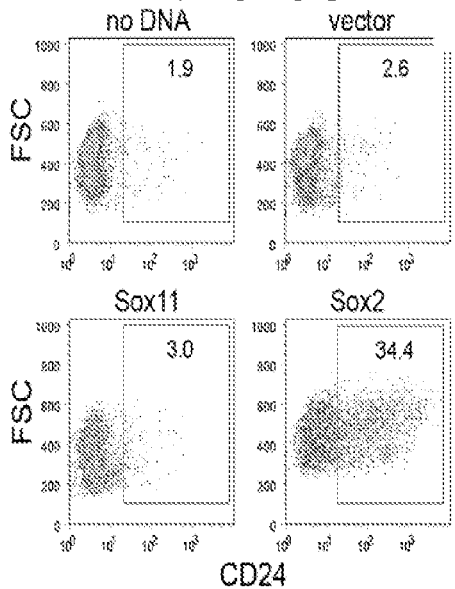
FIG. 9D
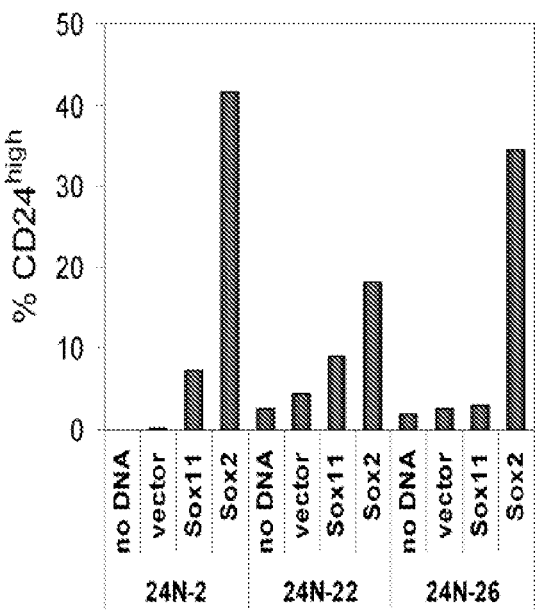

FIG. 10A
FIG. 10B
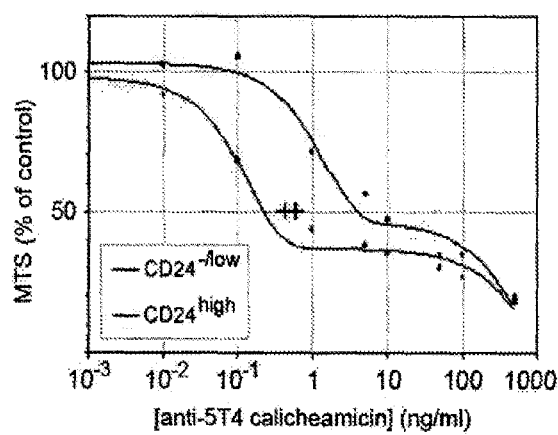
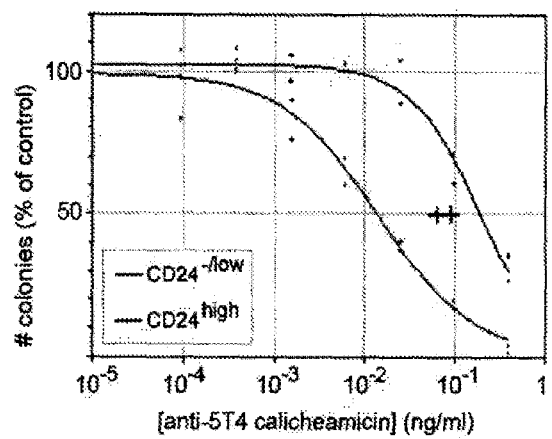

Day after staging

TUMOR-INITIATING CELLS AND METHODS FOR USING SAME

RELATED APPLICATION

This is a national stage application of PCT International Application No. PCT/US2010/028926, which claims priority to U.S. Provisional Application No. 61/164,272, filed 27 Mar. 2009, which is hereby incorporated herein by reference in its entirety.

FIELD OF THE INVENTION

The present invention generally relates to highly tumorigenic cells, also called cancer stem cells or tumor-initiating cells, methods for isolating same and tumor-initiating cell markers for use in said methods. More particularly, the present invention relates to tumor-initiating cells having high levels of 5T4 expression ($5T4^{high}$), optionally with no or low levels of CD24 expression ($CD24^{-/low}$) and with CD44 expression ($CD44^+$). The disclosed tumor-initiating cell populations are useful for identification of new drugs and targets for cancer therapy, and for testing the efficacy of existing cancer drugs.

BACKGROUND OF THE INVENTION

Signaling pathways that regulate self-renewal and differentiation contribute to the cellular heterogeneity within tumors. The varying states of self-renewal and differentiation are evidenced by tumor subpopulations and individual tumor cells that exhibit disparate levels of in vivo tumorigenicity and in vitro clonogenicity. See Lobo et al., *Annu. Rev. Cell Dev. Biol.*, 2007 23: 675-699; Reya et al, *Nature*, 2001, 414: 105-111. The development of new tumor models has begun to enable the characterization of tumor heterogeneity at cellular levels. Implants of solid tumors in immunocompromised mice exhibit a rich architecture that reflects the histology of the original sample but that is not recapitulated in xenografts from cell lines cultured in serum. The culturing of cancer cells in defined serum-free media and/or three-dimensional matrices preserves the physiological characteristics of the cells more than culturing in media with serum (Lee et al., *Cancer Cell*, 2006, 9: 391-403). Fluorescence-activated cell sorting (FACS) of cells from tumors, xenografts, and cell lines has facilitated the molecular characterization of specific tumor sub-populations.

In many tumors, cells defined by specific surface markers form tumors more efficiently than other cells in the same tumor. These cells are alternately referred to as multipotent tumor-initiating cells, cancer stem cells, tumor-initiating cells, and cancer-initiating cells. Tumor-initiating cells were first identified in the hematopoietic system (Bonnet & Dick, *Nat. Med.*, 1997, 3(7): 730-737) and have since been identified in solid tumors, including tumors of the brain, breast, colon, head and neck, lung, melanoma, pancreas, and prostate. See Visvader & Lindeman, *Nat. Rev. Cancer*, 2008, 8: 755-768 and reference cited therein. In a particular tumor type, the same set of cell surface markers can be used to isolate tumor-initiating cells from fresh tumor samples, xenografts, and cell lines. See e.g., Al-Hajj et al., *Proc. Natl. Acad. Sci. USA*, 2003, 100: 3983-3988; Filmore & Kuperwasser, *Breast Cancer Res.*, 2008, 10: R25; Hermann et al., *Cell Stem Cell*, 2007, 1: 313-323. Matsui et al., *Blood*, 2004, 103: 2332-2336. CD44, a marker of tumor-initiating cells in several tumor types, was recently shown to have a direct role in tumorigenesis and to be repressed by p53 (Godar et al., *Cell*, 2008, 134: 62-73).

Tumor-initiating cells show resistance to standard therapies. For example, tumor-initiating cells were highly enriched in samples from breast cancer patients that had received chemotherapy, suggesting an explanation for disease relapse following treatment (Yu et al., *Cell*, 2007, 131: 1109-1123). Similarly, $CD133^+$ tumor-initiating cells in glioblastoma were resistant to irradiation that eradicated the more prevalent $CD133^-$ cells (Bao et al., *Cancer Res.*, 2006, 68: 6043-6048). Thus, in the context of therapy, eliminating tumor-initiating cells might require targeting mechanisms other than those used to target the bulk of the tumor.

To develop treatments that significantly increase long-term patient survival in cancer, tumor-initiating cells responsible for tumor recurrence and metastasis represent an important therapeutic target for this disease. To meet this need, the present invention provides isolated and enriched populations of tumor-initiating cells that can be used to test the efficacy of new and existing cancer drugs.

SUMMARY OF THE INVENTION

The present invention provides isolated and enriched tumor-initiating cell populations. In one aspect of the invention, an isolated tumor-initiating cell population is derived from a tumor cell population, the isolated tumor-initiating cell population comprising at least 90% tumor-initiating cells, wherein the tumor-initiating cells (i) express 5T4 at a level that is at least 2-fold higher than non-tumorigenic cells of the same origin, (ii) are tumorigenic, (iii) are capable of migration, (iv) are capable of self-renewal, and (v) generate tumors comprising non-tumorigenic cells. In another aspect of the invention, an enriched tumor-initiating cell population is provided, which is derived from a tumor cell population comprising tumor-initiating cells and non-tumorigenic cells, and wherein the tumor-initiating cells (i) express 5T4 at a level that is at least 2-fold higher than non-tumorigenic cells of the same origin, (ii) are tumorigenic, (iii) are capable of migration, (iv) are capable of self-renewal, (v) generate tumors comprising non-tumorigenic cells, and (vi) are enriched at least 2-fold compared to the tumor cell population. The isolated or enriched tumor-initiating populations may also express CD24 at a level that is at least 2-fold lower than non-tumorigenic cells of the same origin, and/or express CD44.

Also provided are methods of preparing isolated and enriched tumor-initiating cell populations. For example, a representative method of isolating or enriching a tumor-initiating cell population includes the steps of (a) providing dissociated tumor cells, wherein a majority of the cells express 5T4 at a low level and a minority of the cells express 5T4 at a high level; (b) contacting the dissociated tumor cells with an agent that specifically binds to 5T4; and (c) selecting cells that specifically bind to the agent of (b) to an extent that shows a high level of 5T4 expression that is at least about 2-fold greater than the low level; whereby a tumor-initiating cell population is isolated or enriched. Optionally, the methods for preparing an isolated or enriched 5T4 expressing tunor initiating cell population include the additional steps of contacting the dissociated tumor cells with an agent that specifically binds to CD44; and selecting cells that specifically bind to the agent of to an extent that shows expression of CD44. Optionally, the methods for preparing an isolated or enriched 5T4 expressing tunor initiating cell population may also include the steps of contacting the dissociated tumor cells with an agent that specifically binds to CD24; and selecting cells that specifically bind to the agent of to an extent that shows a low level of CD24 expression that is at least about 5-fold lower than non-tumorigenic cells of the same origin. Alternatively, the tumor initiating cell population can be enriched through culturing the primary tumor cells in serum free conditions. In yet another representative method of the invention, isolating or enriching a 5T4 expressing tumor-initiating cell population can include contacting the dissociated tumor cells with an agent that specifically binds to CD24; and depleting cells that specifically bind to the agent of to an extent that shows a high level of CD24 expression that is at least about 5-fold greater than non-tumorigenic cells of the same origin.

Still further are provided methods of testing efficacy of a cancer drug or candidate cancer drug using the disclosed isolated or enriched tumor-initiating cell populations. For example, such methods can include the steps of (a) providing an isolated or enriched tumor-initiating cell population; (b) contacting the tumor-initiating cells with a cancer drug or a candidate cancer drug; (c) observing a change in tumorigenic potential of the tumor-initiating cells following contacting the tumor-initiating cells with the cancer drug or candidate cancer drug.

BRIEF DESCRIPTION OF THE DRAWINGS

FIG. 1A shows the results of flow cytometric analysis using expression of CD24 and CD44. Distinct populations of H460T were revealed by flow cytometry and labeling with anti-CD24 and anti-CD44 antibodies.

FIG. 1B shows mice that received subcutaneous implants of $CD24^{-/low}CD44^+$ cells or $CD24^{high}CD44^+$ cells. Arrows, sites of implantation.

FIG. 1C is a line graph showing a quantitative analysis results of the observation in FIG. 1B. Values indicate the average tumor measurement ±SEM (standard error of the mean).

FIG. 1D is a line graph showing CD44 tumorigenesis based upon CD44 expression in H460T cells. $CD24^{-/low}CD44^{high}$ and $CD24^{-/low}CD44^{low}$ cells were sorted and implanted subcutaneously into mice. Values indicate the average tumor measurement ±SEM.

FIG. 1E a line graph showing spheroid growth of sorted populations. FACS-isolated $CD24^{-/low}$ $CD44+$ or $CD24^{high}$ $CD44^+$ cells were cultured in suspension for 5 days to promote spheroid formation. Spheroids of 0.2 mm diameter were transferred to individual wells of a 24-well plate and measured over a two-week time course. Values indicate the average spheroid volume±SD (standard deviation of the mean).

FIG. 1F a line graph showing the differential response of $CD24^{-/low}CD44^{high}$ and $CD24^{-/low}$ $CD44^{low}$ populations to mTOR inhibitor CCI-779.

FIG. 1G is a bar graph showing the results of a transwell migration assay. $CD24^{-/low}CD44^+$ cells migrated efficiently in response to serum. The $CD24^{-/low}CD44^+$ value shows the average cell number normalized to $CD24^{high}CD44^+$ for each experiment (±SD (n=4)).

FIG. 1H shows micrographs depicting efficient migration on fibronectin of $CD24^{-/low}CD44^+$ spheroids 72 hours after spheroids were placed on fibronectin-coated slides.

FIG. 2A shows the results of flow cytometric analysis of $CD24^{-/low}CD44^+$ cells and $CD24^{high}CD44^+$ following a three week culture. Distinct populations are revealed based upon CD24 and CD44 expression.

FIG. 2B shows the results of flow cytometric analysis of CD24 and CD44 expression in a representative tumor from sorted $CD24^{-/low}CD44^+$ cells.

FIG. 2C shows the results of flow cytometric analysis of CD24 and CD44 expression in clonal lines established from single sorted $CD24^{-/low}CD44^+$ or $CD24^{high}CD44^+$ cells. The proportion of $CD24^{high}$ cells in the transitioning $CD24^{-/low}$ clones ranged from 10-70% depending on the clone. The CD24 distribution in each clone was steady over months in culture.

FIG. 2D a line graph showing tumor growth from clonal lines presented in FIG. 2C. $CD24^{-/low}$ cells were sorted from $CD24^{-/low}$ clones and $CD24^{high}$ cells were sorted from $CD24^{high}$ clones. Values indicate the average tumor measurement ±SEM. Tr, transitioning clone; St, stable clone.

FIG. 2E a line graph showing tumor growth of $CD24^{-/low}$ and $CD24^{high}$ cells FACS-isolated from transitioning $CD24^{-/low}$ clones. Values indicate the average tumor measurement ±SEM.

FIG. 3A is a schematic drawing of the experimental design. Sorted cells were labeled with 2.5 µM CFSE (Invitrogen of Carlsbad, Calif., USA), washed extensively, and then plated with another sorted population in the ratio of the parent population (1 $CD24^{-/low}CD44^+$ to 3 $CD24^{high}CD44^+$). CFSE at 2.5 µM had little or no effect on the growth of H460T cells over the time course of this experiment. After three days, cultures were analyzed for CD24, and the initial populations could be distinguished based on CFSE.

FIG. 3B shows the results of flow cytometric analysis of labeled and unlabeled populations cultured individually or in combination.

FIG. 3C is a histogram of replicate experiments shown in FIG. 3B. The transition of $CD24^{-/low}CD44^+$ cells to $CD24^{high}CD44^+$ was comparable when the cells were cultured alone or co-cultured with $CD24^{high}CD44^+$ or $CD24^{-/low}CD44^+$ cells. The stability of the $CD24^{high}CD44^+$ phenotype was observed when $CD24^{high}CD44^+$ cells were cultured alone or co-cultured with $CD24^{-/low}CD44^+$ or $CD24^+$ or $CD24^{high}CD44^+$ cells.

FIG. 4A shows the results of flow cytometric analysis of HCC2429 based on CD24 expression.

FIG. 4B is a line graph showing differential tumorigenicity of $CD24^{-/low}CD44^+$ or $CD24^{high}CD44^+$ HCC2429 populations. Values indicate the average tumor measurement ±SEM.

FIG. 4C shows the results of flow cytometric analysis of $CD24^{-/low}CD44^+$ or $CD24^{high}CD44^+$ populations 2 weeks after sorting. Cultured $CD24^{-/low}CD44^+$ cells can transition to $CD24^{high}CD44^+$, but $CD24^{high}CD44^+$ do not transition to $CD24^{-/low}CD44^+$ cells.

FIG. 6A is a bar graph showing 5T4 (TPBG) mRNA levels on Affymetrix GENECHIP® oligonucleotide arrays hybridized with mRNA transcripts prepared from CD24$^{-/low}$CD44+ and CD24$^{high}$CD44$^+$ cells. Values indicate the average of triplicate samples±SD.

FIG. 6B shows the results of immunoblot analysis to detect 5T4 expression in CD24$^{-/low}$CD44+ and CD24$^{high}$CD44$^+$ cells grown in media or treated with vehicle or all-trans retinoic acid.

FIG. 7A shows micrographs of the 87426 primary culture of NSCLC under conditions that promote growth (left) and differentiation at the air-liquid interface (right). Scale bars, 200 μM.

FIG. 7B shows the results of immunoblot analysis to detect 5T4 expression at the indicated time points during differentiation.

FIG. 7C shows mRNA levels on Affymetrix GENECHIP® oligonucleotide arrays hybridized with mRNA transcripts prepared from primary culture lung cancer cells under conditions of growth or differentiation. Values represent averages±SD. FN1, fibronectin; VIM, vimentin.

FIG. 7D shows the results of gene profiling experiments to compare gene expression in the cell line culture (H460T) and primary culture (87426A1) tumor models. See Example 3. The expression difference for genes that are above noise level in the H460T data set were compared. Statistical analysis yielded the False Discovery Rate of 0.0015.

FIG. 7E is a bar graph showing mRNA levels of CD24 and CD44 in serum-free primary culture of 87426 cells at days 0, 12, and 24 of differentiation. Cultures were maintained in BEBM growth medium or differentiated for 12 and 24 days in CnT-23 medium containing 50 nM retinoic acid and 1 mM CaCl$^2$, without exposing cells to the air-liquid interface.

FIG. 7F shows the distribution of CD24 and CD44 expression in duplicate samples from the experiment presented in in FIG. 7D. After 12 days of differentiation as a monolayer culture, the levels of cell surface CD24 expression increased and were retained up to 24 days. Cell surface levels of CD44 expression were decreased by 12 days and declined further by 24 days of differentiation.

FIG. 7G is a bar graph showing mRNA levels of angiogenesis factors in serum-free primary culture of 87426 cells at day 0, 12, and 24 of differentiation. The levels of mRNA were determined using gene expression profiling as described in Example 6.

FIG. 8A shows flow cytometric analysis of 5T4 expression in dissociated xenografts from the 37622 line (left panel), cultured cells established from 37622 xenografts in serum-free medium (middle panel; shown after five weeks in culture), and in xenografts of implanted cells of the serum-free culture (right panel).

FIG. 8B is a table showing tumor incidence in animals that were implanted with 5T4$^{high}$ or 5T4$^{low}$ cells from dissociated 37622 or 60257 xenografts (#1, #2 indicate replicate experiments).

FIGS. 9A-9D show that Sox-2 induces differentiation of CD24$^{-/low}$ cells.

FIG. 9A is a bar graph showing Sox-2 mRNA levels from Affymetrix GENECHIP® oligonucleotide arrays hybridized with transcripts prepared from CD24$^{-/low}$ clones.

FIG. 9B shows the results of immunoblot analysis to detect Sox-2 and Sox-11 transcripts in stable CD24$^{-/low}$ clones transfected with Sox-2-Flag, Sox-11-Flag, empty vector, or no DNA. Cells were harvested 24 hours after transfection and subjected to immunoblot with anti-Flag (top) or anti-β-actin antibody.

FIG. 9C shows the results of flow cytometric analysis of CD24 in stable CD24$^{-/low}$ clones transfected with Sox-2-Flag, Sox-11-Flag, empty vector, or no DNA after three weeks in culture.

FIG. 9D is a histogram of the data presented in FIG. 9C showing the percentage of CD24$^{high}$ cells in each sample.

FIGS. 10A-10B show sensitivity of CD24$^{-/low}$CD44$^+$ cells to an anti-5T4-calicheamicin conjugate. CD24$^{high}$CD44$^+$ cells are labeled "CD24$^{-/low}$" and CD24$^{high}$CD44$^+$ cells are labeled "CD24$^{high}$".

FIG. 10A is a line graph showing the results of a four-day MTS assay. Crosshairs indicate the sensitivity to free calicheamicin.

FIG. 10B is a line graph showing the results of a clonogenic assay. Crosshairs indicate the sensitivity to free calicheamicin.

FIG. 12A is a line graph showing tumor volume regression of 37622 xenografts following treatment with anti-5T4 antibody-calicheamicin conjugate. Animals were administered anti-5T4 antibody-calicheamicin conjugate on days 1, 5, and 9 after staging. Values indicate average tumor volume ±SEM.

FIG. 12B a line graph showing tumor volume regression of 60274 xenografts following treatment with anti-5T4 antibody-calicheamicin conjugate. Animals were administered anti-5T4 antibody-calicheamicin conjugate on days 1, 5, and 9 after staging. Values indicate average tumor volume ±SEM.

FIG. 12C a line graph showing tumor volume regression of 60274 xenografts following treatment with anti-5T4 antibody-calicheamicin conjugate. Animals were administered anti-5T4 antibody-calicheamicin conjugate on days 1, 5, and 9 after staging. Values indicate average tumor volume ±SEM.

DETAILED DESCRIPTION OF THE INVENTION

Figure 1A:
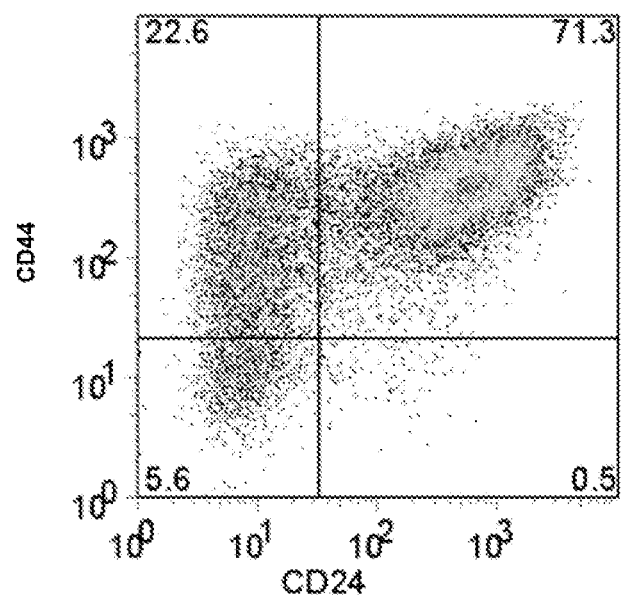
FIGS. 1A-1H show that the $CD24^{-/low}CD44^+$ cell phenotype marks tumor-initiating cells in the H460T non-small cell lung cancer line (NSCLC). $CD24^{-/low}CD44+$ cells are labeled "$CD24^{-/low}$" and $CD24^{high}CD44^+$ cells are labeled "$CD24^{high}$".

The present invention provides methods for the prospective identification of tumor-initiating cells that express the oncofetal antigen 5T4 and optionally, also express CD44 and low levels of CD24. These cells are highly tumorigenic in vitro and in vivo are self-renewing, are capable of migration, and have the ability to differentiate. The disclosed tumor-initiating cell populations may also show apoptosis resistance and contribute to cancer relapse and metastasis. Also provided are methods for isolating tumor-initiating cell populations and for enriching tumor-initiating cells within a population. Still further are provided novel tumor-initiating cell markers.

The tumor-initiating cell populations disclosed herein are useful for studying the effects of therapeutic agents on tumor growth, relapse, and metastasis. Isolated tumor-initiating cells can be used to identify unique therapeutic targets, which can be used to generate antibodies that target tumor-initiating cells. The isolated tumor-initiating cells can also be used in screening assays to improve the probability that drugs selected based upon in vitro activity, or based upon cytotoxicity of tumor populations that include non-tumorigenic cells, will successfully eradicate disease and prevent relapse in vivo. Tumor-initiating cells isolated from patients may also be used to predict disease outcome and/or sensitivity to known therapies.

I. Tumor-Initiating Cells

A tumor-initiating cell is known in the art to mean a cell (1) that is capable of generating one or more kinds of progeny with reduced proliferative or developmental potential (e.g., differentiated cells); (2) that has extensive proliferative capacity; and (3) that is capable of self-renewal or self-maintenance. See e.g., Potten et al., *Development,* 1990, 110; 1001-1020. Thus, tumor-initiating cells share properties of stem cells found in adult tissues, (including cells of the blood, gut, breast ductal system, and skin) that constantly replenish cells lost during normal tissue functions.

The best-known example of adult cell renewal by the differentiation of stem cells is the hematopoietic system. Developmentally immature precursors such as hematopoietic stem cells and progenitor cells respond to molecular signals gradually forming the varied blood and lymphoid cell types. Stem cells are also found in other tissues, including epithelial tissues (Slack, *Science,* 2000, 287: 1431-1433) and mesenchymal tissues (U.S. Pat. No. 5,942,225). Cancer stem cells may arise from any of these cell types, for example, because of genetic damage in normal stem cells or by the dysregulated proliferation of stem cells and/or differentiated cells.

Tumor-initiating cells of the present invention may be derived from any cancer comprising tumorigenic stem cells, i.e., multipotent cells having an ability to proliferate extensively or indefinitely, and which give rise to the majority of cancer cells. Within an established tumor, most cells have lost the ability to proliferate extensively and form new tumors, and a small subset of tumor-initiating cells proliferate to thereby regenerate the tumor-initiating cells as well as give rise to tumor cells lacking tumorigenic potential. Tumor-initiating cells may divide asymmetrically and symmetrically and may show variable rates of proliferation.

In contrast to tumor-initiating cells, non-tumorigenic tumor cells fail to form a palpable tumor upon transplantation into an immunocompromised host, wherein if the same number of non-fractionated, dissociated cancer cells were transplanted under the same circumstances, the tumor-initiating cells would form a palpable tumor in the same period. A palpable tumor is known to those in the medical arts as a tumor that is capable of being handled, touched, or felt. Non-tumorigenic cells also show decreased migration as compared to tumor-initiating cells, an inability to generate tumor-initiating cells, and increased expression of differentiation markers.

Representative cancers from which tumor-initiating cells may be isolated include cancers characterized by solid tumors, including 5T4-expressing tumors such as lung, ovarian, colorectal, and gastric tumors. Additional representative cancers from which tumor-initiating cells may be isolated include acoustic neuroma, acute lymphoblastic leukemia, acute myelogenous leukemia, acute myeloid leukemia, adenocarcinoma, adenosqaumous carcinoma, adrenocortical carcinoma, AIDS-related lymphoma, anal cancer, angiosarcoma, astrocytoma, B cell lymphomas and leukemias, basal cell carcinoma, basaloid carcinoma, bile duct cancer, bile duct carcinoma, bladder cancer, bladder carcinoma, brain tumor, breast cancer, bronchogenic carcinoma, bulky disease NHL and Waldenstrom's Macroglobulinemia, carcinosarcoma, cerebellar astrocytoma, cerebral astrocytoma, cervical cancer, chondrosarcoma, chordoma, choriocarcinoma, chronic leukocytic leukemia, chronic lymphocytic leukemia, chronic myelogenous leukemia, clear cell carcinoma, colon cancer, colorectal cancer, craniopharyngioma, cutaneous T-cell lymphoma, cystadenocarcinoma, embryonal carcinoma, endometrial cancer, endotheliosarcoma, ependymoma, epithelial carcinoma, esophageal cancer, Ewing's sarcoma, Ewing's tumor, fibrosarcoma, gallbladder cancer, gestational trophoblastic tumor, giant cell carcinoma, glioma, hairy cell leukemia, hemangioblastoma, hemangiomas of infancy and childhood, hematopoietic malignancies, hematopoietic malignancies including acute lymphoblastic leukemia, hepatoma, high grade immunoblastic NHL, high grade lymphoblastic NHL, high grade small non-cleaved cell NHL, Hodgkin's lymphoma, hypopharyngeal cancer, including but not limited to low grade/follicular non-Hodgkin's lymphoma (NHL), intermediate grade diffuse NHL, intermediate grade/follicular NHL, islet cell carcinoma. Kaposi's sarcoma, kidney cancer, large cell carcinoma with rhabdoid phenotype, large cell lung carcinoma, laryngeal cancer, leiomyosarcoma, liposarcoma, liver cancer, lung cancer, lung carcinoma, lymphangioendotheliosarcoma, lymphangiosarcoma, lymphoblastic leukemia, lymphocytic leukemia, lymphoepitheliomalike carcinoma, malignant melanoma, malignant mesothelioma, malignant thymoma, medullary carcinoma, medulloblastoma, melanoma, meningioma, mesothelioma, monocytic leukemia, multiple myeloma, mycosis funoides, myelogenous leukemia, myxosarcoma, nasopharyngeal cancer, neuroblastoma, non-Hodgkin's lymphoma, non-small cell lung carcinoma, oligodendroglioma, oral cancer, oropharyngeal cancer, osteogenic sarcoma, osteosarcoma, ovarian cancer, ovarian epithelial cancer, ovarian germ cell tumor, pancreatic cancer, pancreatic carcinoma, papillary adenocarcinomas, papillary carcinoma, parathyroid cancer, penile cancer, pinealoma, pituitary tumor, promyelocytic leukemia, prostate cancer, prostate cancer, pulmonary blastoma, rectal cancer, renal cell carcinoma, retinoblastoma, rhabdomyosarcoma, salivary gland cancer, sarcomas, sebaceous gland carcinoma, seminoma, skin cancer, small cell lung cancer, small cell lung carcinoma, small intestine cancer, small lymphocytic (SL) NHL, soft tissue sarcoma, squamous cell carcinoma, squamous cell lung carcinoma, stomach cancer, sweat gland carcinoma, synovioma, testicular cancer, thyroid cancer, uterine cancer, uterine sarcoma, vaginal cancer, vulvar cancer, and Wilm's tumor.

Tumor-initiating cells may also be derived from cells associated with a proliferative disease, i.e., a class of diverse disorders and diseases characterized by a lack of control or poorly controlled cell division or proliferation. Proliferative diseases include disorders associated with an overgrowth of connective tissues, such as various fibrotic conditions, including scleroderma, arthritis, juvenile arthritis, gouty arthritis, and liver cirrhosis, and conditions such as restenosis, arteriosclerosis, and proliferative diabetic retinopathy.

I.A. Tumor-Initiating Cell Markers

Tumor-initiating cells may be selected using positive and negative molecular markers. A reagent that binds to a tumor-initiating cell positive marker (i.e., a marker expressed by tumor-initiating cells at elevated levels compared to non-tumorigenic or differentiated cells) can be used for the selection of tumor-initiating cells. Positive markers for tumor-initiating cells may also be present on non-tumorigenic cancer cells, i.e., cancer cells other than tumor-initiating cells, but at reduced levels. Markers that are widely expressed may show a measurable change in expression level in tumor-initiating cells and/or may provide for resolution of tumor-initiating cells when used in combination with additional positive or negative markers. A reagent that binds to a tumor-initiating cell negative marker (i.e., a marker not expressed or expressed at measurably reduced levels by tumor-initiating cells can be used for the elimination of those tumor cells in the population that are not tumor-initiating cells. For selection using positive and negative molecular markers, useful markers include those that are expressed on the cell surface such that live cells are amenable to sorting and tracking.

When assessing expression levels using techniques such as immunoblot, tumor-initiating cell positive markers are typically expressed at a level that is at least about 2-fold greater than differentiated cells of the same origin or non-tumorigenic cells, for example, at least about 4-fold greater, or at least about 5-fold greater, or at least about 8-fold greater, or at least about 10-fold greater, or at least about 15-fold greater, or at least about 20-fold greater, or at least about 50-fold greater, or at least about 100-fold greater. When assessing expression levels using flow cytometry, tumor-initiating cell positive markers are typically expressed at a level that is at least about 0.5 log greater than differentiated cells of the same origin or non-tumorigenic cells, for example, at least about 1 log greater, at least about 1.5 logs greater, at least about 2 logs greater, or at least about 3 logs greater. Conversely, when assessing expression levels using techniques such as immunoblot, tumor-initiating cell negative markers are typically expressed at a level that is at least about 2-fold less than differentiated cells of the same origin or non-tumorigenic cells, for example, at least about 4-fold less, or at least about 8-fold less, or at least about 10-fold less, or at least about 15-fold less, or at least about 20-fold less, or at least about 50-fold less, or at least about 100-fold less. When assessing expression levels using flow cytometry, tumor-initiating cell negative markers are typically expressed at a level that is at least about 0.5 log less than differentiated cells of the same origin or non-tumorigenic cells, for example, at lease about 1 log less, at least about 1.5 logs less, at least about 2 logs less, or at least about 3 logs less.

Disclosed herein are 5T4, CD44, and CD24 markers that can be used alone or in combination for the prospective identification and isolation of tumor-initiating cells from lung. Expression of 5T4 and CD44 are positive markers, whereas expression of CD24 is a negative marker. Thus, tumor-initiating cells of the invention include those expressing high levels of 5T4 ($5T4^{hi}$), moderate to high levels of CD44 ($CD44^+$), and/or little or no expression of CD24 ($CD24^{-/lo}$).

5T4 oncofetal antigen is a 72 kDa highly glycosylated transmembrane glycoprotein comprising a 42 kDa non-glycosylated core (Hole et al., Br. J. Cancer, 1988, 57: 239-46; Hole et al., Int. J. Cancer, 1990, 45: 179-84; PCT International Publication No. WO89/07947: U.S. Pat. No. 5,869,053). Human 5T4 is expressed in numerous cancer types, including carcinomas of the bladder, breast, cervix, endometrium, lung, esophagus, ovary, pancreas, stomach, and testes, and is substantially absent from normal tissues, except for syncytiotrophoblast in placenta (see, e.g., Southall et al., Br. J. Cancer, 1990, 61: 89-95 (immunohistological distribution of 5T4 antigen in normal and malignant tissues); Mieke et al., Clin. Cancer Res., 1997, 3: 1923-1930 (low intercellular adhesion molecule 1 and high 5T4 expression on tumor cells correlate with reduced disease-free survival in colorectal carcinoma patients); Starzynska et al. Br. J. Cancer, 1994, 69: 899-902 (prognostic significance of 5T4 oncofetal antigen expression in colorectal carcinoma); Starzynska et al., Br. J. Cancer, 1992, 66: 867-869 (expression of 5T4 antigen in colorectal and gastric carcinoma); Jones et al., Br. J. Cancer, 1990, 61: 96-100 (expression of 5T4 antigen in cervical cancer); Connor & Stern, Int. J. Cancer, 1990, 46: 1029-1034 (loss of MHC class-I expression in cervical carcinomas); Ali et al., Oral Oncology, 2001, 37: 57-64 (pattern of expression of the 5T4 oncofetal antigen on normal, dysplastic and malignant oral mucosa); PCT International Publication No. WO89/07947; U.S. Pat. No. 5,869,053). For example, tissues reported to have no expression of 5T4 include the liver, skin, spleen, thymus, central nervous system (CNS), adrenal gland, and ovary. Tissues reported to have focal or low expression of 5T4 include the liver, skin, spleen, lymph node, tonsil, thyroid, prostate, and seminal vesicles. Weak-moderate diffuse expression of 5T4 has been reported in the kidney, lung, pancreas, pharynx, and gastro-intestinal tract. The only tissue reported to have high expression of 5T4 is syncytiotrophoblast, and 5T4 was also absent from normal serum or the serum of pregnant women (i.e., levels<10 ng/ml). Overexpression of 5T4 in tumors has been correlated with disease progression, and assessment of 5T4 expression has been suggested as a useful approach for identifying patients with poor prognosis. See, e.g., Mulder et al., Clin. Cancer Res., 1997, 3: 1923-1930; Naganuma et al., Anticancer Res., 200, 22: 1033-1038; Starzynska et al., Br. J. Cancer, 1994, 69: 899-902; Starzynska et al., Eur. J. Gastroenterol. Hepatol., 1998, 10: 479-484; Wrigley et al., Int. J. Gynecol. Cancer, 1995, 5: 269-274.

CD44 is a transmembrane glycoprotein that participates in cancer metastasis by modulating cell adhesiveness, motility, matrix degradation, proliferation, and/or cell survival. See e.g., Marhaba & Zoller, J. Mol. Histol., 2004, 35(3): 211-231. CD24 antigen is a cell surface glycoprotein marker of differentiation that is used as a negative marker, i.e., tumor-initiating cells show little or no CD24 expression ($CD24^{-/low}$). Alone or in combination, cells expressing CD44 and $CD24^{-/low}$ have been used to identify tumor-initiating cells in many tumor types, including tumors of the breast, colon, head and neck, and pancreas. See e.g., Al-Hajj et al., Proc. Natl. Acad. Sci. USA, 2003, 100: 3983-3988; Yu et al., Cell, 2007, 131: 1109-1123; Dalerba et al., Proc. Natl. Acad. Sci. USA, 2007, 104: 10158-10163; Prince et al., Proc. Natl. Acad. Sci. USA, 2007, 104: 973-978; and Li et al., Cancer Res., 2007, 67: 1030-1037.

Figure 7A:
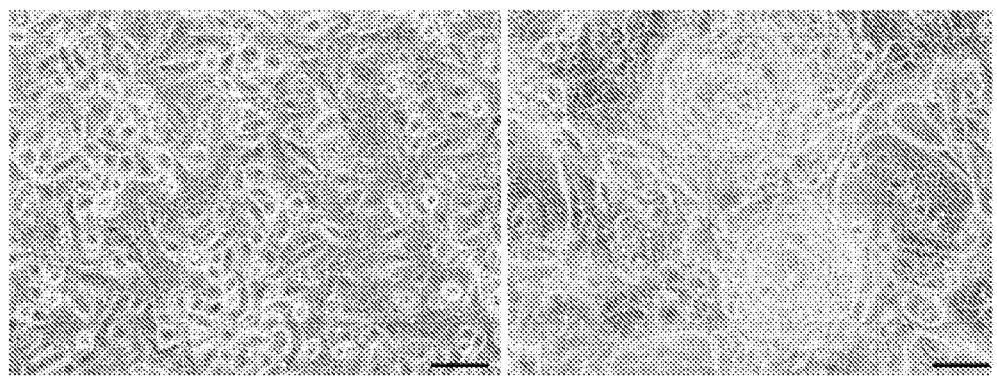
FIGS. 7A-7G show gene expression profiles associated with undifferentiated and differientiated 87426 primary culture cells.
Figure 7B:
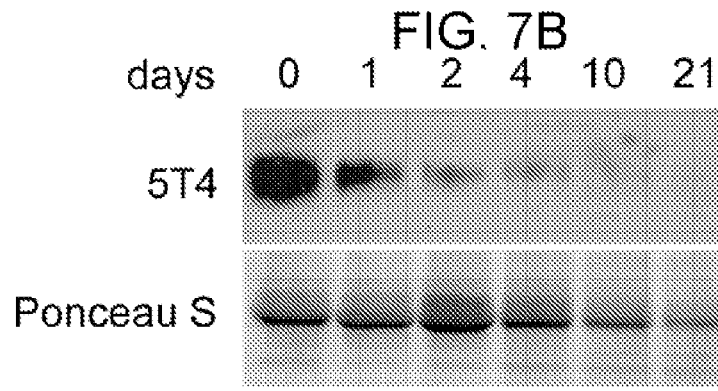
Figure 7C:
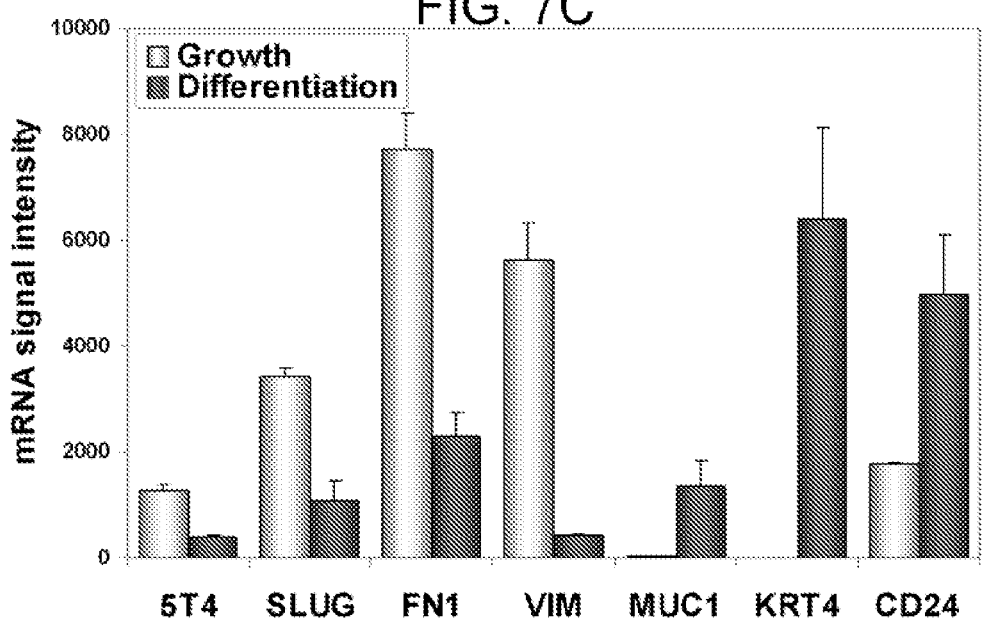
Figure 7D:
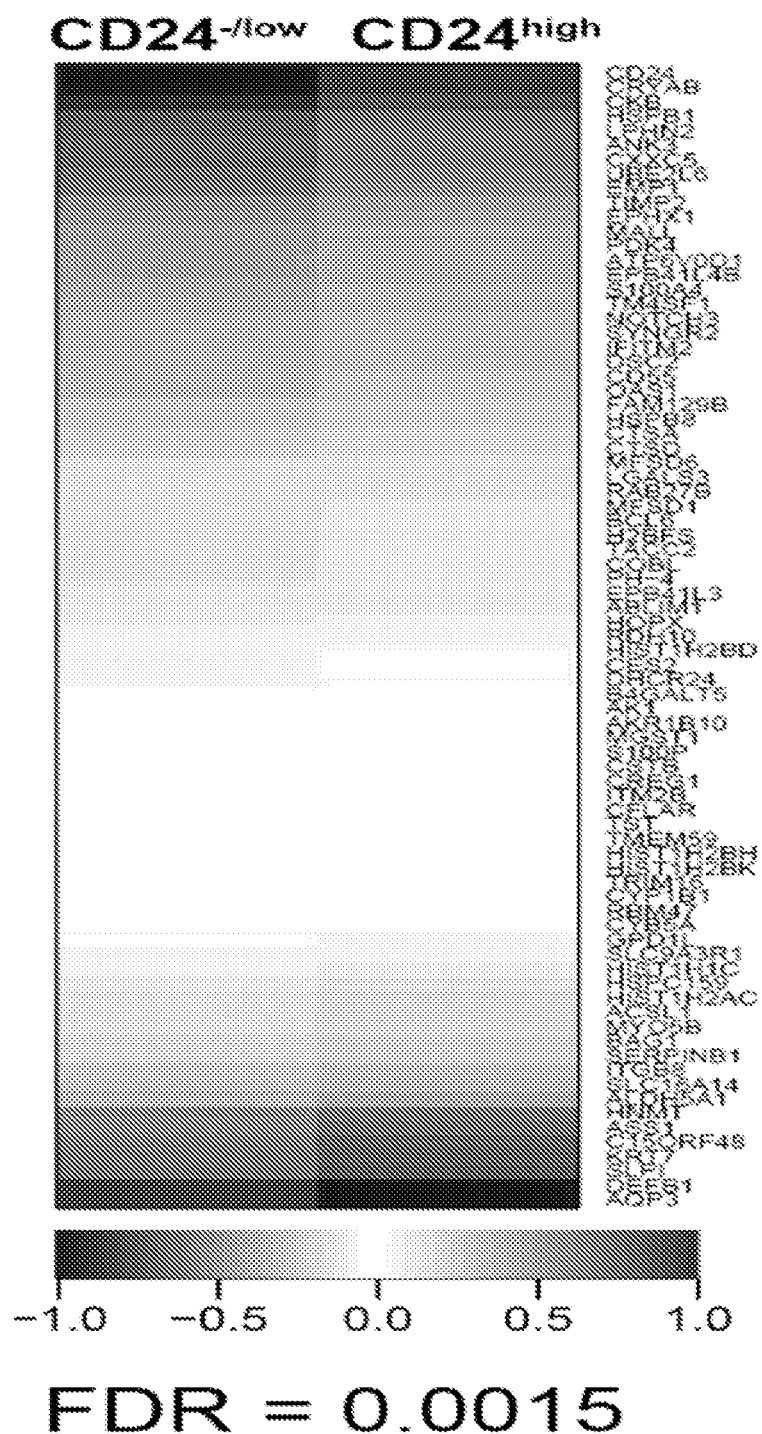
Figure 7E:
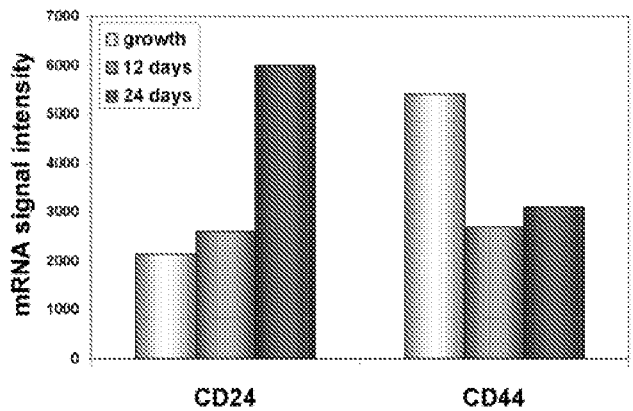
Figure 7F:
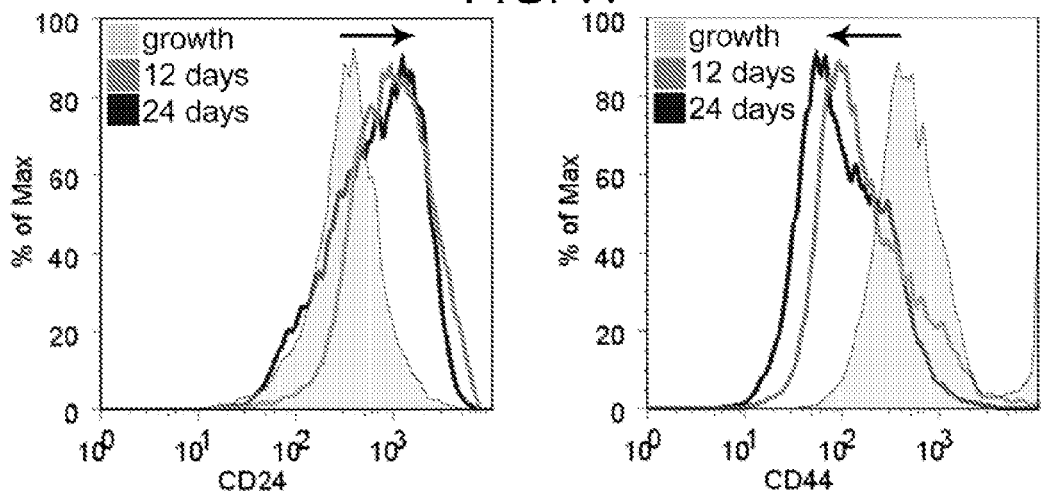

In addition to the 5T4 and CD44+ markers described herein, other potential tumor-initiating cell positive markers in lung cancer include SLUG, fibronectin (FN1), and vimentin (VIM) (see FIG. 7C); vascular endothelial growth factor A (VEGF-A), vascular endothelial growth factor B (VEGF-B); vascular endothelial growth factor C (VEGF-C); platelet derived growth factor (PDGF), and insulin-like growth factor-I (PIGF) (see FIG. 7F); CD133 (see Eramo et al., Cell Death Differ., 2008, 15: 504-514), and CD117 (Donnenberg et al., J. Control Release, 2007, 122(3): 385-391). Representative additional potential positive tumor-initiating cell markers in lung cancer include transforming growth factor β type III receptor (TGFβRIII), netrin receptor UNC5D (Unc5D), patatin-like phospholipase domain-containing protein 4 (PNPLA4), inward rectifier potassium channel 2 (KCNJ2), gamma-aminobutyric acid (GABA) A receptor; beta 3 (GABRB3), dihydropyrimidine dehydrogenase (DPYD), sperm associated antigen 1 (SPAG1), intestinal cell (MAK-like) kinase (ICK), stanniocalcin 2 (STC2), defensinβ1 (Defβ1), and FLJ38736. See Example 5.

Still additional positive tumor-initiating cell markers include CD133 (Bao et al., *Nature,* 2006, 444: 756-760; O'Brien et al., *Nature,* 2007, 445: 106-110; Ricci-Vitiani et al., *Nature,* 2007, 445: 111-115; and Hermann et al., *Cell Stem Cell,* 2007, 1: 313-323), ALDH1 (Yu et al., Cell 2007, 131: 1109-1123), EpCAM$^{high}$ (Dalerba et al., *Proc. Natl. Acad. Sci. USA,* 2007, 104: 10158-10163); epithelial-specific antigen (ESA, Li et al., *Cancer Res.,* 2007, 67: 1030-1037); CD90 (Li et al., *Cancer Res.,* 2007, 67: 1030-1037); ABCG5 (Schatton et al., *Nature,* 2008, 451: 345-349); ABCG2 (Patrawala et al., *Cancer Res.,* 2005, 65(14): 6207-6219; Kondo et al., *Proc. Natl. Acad. Sci. U.S.A.,* 2004, 101(3): 781-786): VEGF receptor-1 (VEGFR-1), VEGFR-2, VEGFR-3, and platelet derived growth factor (PDGF) (see FIG. 7F and Andersen et al., *J. Thorac. Oncol.,* 2009, [Epub ahead of print]); neuron-specific enolase (NSE), cytokeratin 19 fragment (CYFRA), Carcinoembryonic antigen (CEA), squamous cell carcinoma antigen (SCC), CA 125, CA 15.3 and TAG-72.3 (see Molina et al., *Tumour Biol.,* 2008, 29(6): 371-380); VLA-2, Tweak (TNF-like weak inducer of apoptosis), EphB2, EphB3, human Sca-1 (BIG1), CD34, β1 integrin (CD29), CD150, CXCR4, and members of gene sets that are inversely correlated with differentiated primary culture as set forth in Tables 1 and 2. See Examples 3 and 5.

Markers that may be used for selection of tumor-initiating cells based upon low or negative expression include any gene expressed in differentiated or non-tumorigientic cells. Numerous such molecules are known in the art. In addition to the CD24$^{-/low}$ marker described herein, additional lung cancer tumor-initiating cell negative markers include MUC1/CD227 and cytokeratin 4 (KRT4) (see FIG. 7C and Kuemmel et al., *Lung Cancer,* 2009, 63(1): 98-105). Still additional makers useful for isolation or enrichment of lung cancer tumor-initiating cells include CEA, SLX, CYFRA, SCC, progastrin-releasing peptide (ProGRP). See Komagata & Yondea, *Gan To Kagaku Ryoho,* 2004, 31(10): 1609-1613. Additional representative markers that may be used for selection of tumor-initiating cells based upon low or negative expression include members of gene sets that are correlated with differentiated primary culture as set forh in Tables 1 and 2. See Examples 3 and 5.

The above-noted markers can also be use for identification of tumor-initiating cells in cancers other than lung cancer.

In the case of colon or colorectal cancer or other cancers, additional positive markers that may be useful for identification of tumor-initiating cells include prostaglandin F2 receptor regulatory protein (PTGFRN), CD166 (or activated leukocyte adhesion molecule, ALCAM), CD164, CD82, transforming growth factor beta receptor 1 (TGFBR1), MET, ephrin-B2 (EFNB2), integrin alpha 6 (ITGA6; CD49f), teratocarcinoma-derived growth factor 1 (TDGFI), heparin-binding EGF-like growth factor (HBEGF), ABC family transporter ABCC4, ABC family transporter ABCD3, tumor-differentially-expressed gene 2 (TDE2), integrin beta 1 (ITGB1), tumor necrosis factor receptor superfamily 21 (TNFRSF21), CD81 and CD9 (members of the transmembrane-4 superfamily (TM4SF or tetraspanins)), KIAA1324, carcinoembryonic antigen-related cell adhesion molecule 6 (CEACAM6), FZD6 and FZD7 (Wnt receptors), BMPR1A, JAG1, integrin alpha V (ITGAV), NOTCH2, SOX4, HES1, HES6, atonal homolog 1 (ATOH1), E-cadherin (CDH1), Eph receptor B2 (EPHB2), v-myb myeloblastosis viral oncogene homolog (MYB), MYC, SOX9, PCGF1, PCGF4, PCGF5, ALDH1A1, and STRAP. An additional negative marker useful for identification of tumor-initiating cells in colon or colorectal cancer is T cell factor 4 (TCF4). See e.g., PCT International Publication No. WO 07/053648.

In a particular aspect of the invention, isolated tumor-initiating cell population comprises a majority of cells expressing 5T4 at a level that is at least about 2-fold higher than non-tumorigenic cells of the same origin. Tumor-initiating cells may also express 5T4 at a level that is at least about 4-fold higher than non-tumorigenic cells of the same origin, for example, at least about 5-fold higher, or at least about 8-fold higher, or at least about 10-fold higher, or at least about 15-fold higher, or at least about 20-fold higher, or at least about 50-fold higher, or at least about 100-fold higher. When 5T4 expression is assessed using flow cytometry, tumor-initiating cells may also express 5T4 at a level that is at least about 0.5 log higher than non-tumorigenic cells of the same origin, for example, at least about 1 log higher, or at least about 1.5 logs higher, or at least about 2 logs higher, or at least about 3 logs higher.

In another aspect of the invention, the tumor-initiating cell population comprises a majority of cells that express CD24 at a level that is at least about 2-fold lower than CD24$^+$ non-tumorigenic cells of the same origin. Tumor-initiating cells may also express CD24 at a level that is at least about 4-fold lower than non-tumorigenic cells of the same origin, for example, at least about 5-fold lower, or at least about 8-fold lower, or at least about 10-fold lower, or at least about 15-fold lower, or at least about 20-fold lower, or at least about 50-fold lower, or at least about 100-fold lower. When CD24 expression is assessed using flow cytometry, tumor-initiating cells may also express CD24 at a level that is at least about 0.5 log lower than CD24$^+$ non-tumorigenic cells of the same origin, for example, at least about 1 log lower, or at least about 1.5 logs lower, or at least about 2 logs lower, or at least about 3 logs lower.

The tumor-initiating cell population can also comprise a majority of cells that express CD44 at a level that is at least about 2-fold higher than non-tumorigenic cells of the same origin. Tumor-initiating cells may also express CD44 at a level that is at least about 4-fold higher than non-tumorigenic cells of the same origin, for example, at least about 5-fold higher, or at least about 8-fold higher, or at least about 10-fold higher, or at least about 15-fold higher, or at least about 20-fold higher, or at least about 50-fold higher, or at least about 100-fold higher. When CD44 expression is assessed using flow cytometry, tumor-initiating cells may also express CD44 at a level that is at least about 0.5 log higher than non-tumorigenic cells of the same origin, for example, at least about 1 log higher, or at least about 1.5 logs higher, or at least about 2 logs higher, or at least about 3 logs higher.

An isolated tumor-initiating cell population is removed from its natural environment (such as in a solid tumor) and is at least about 75% free of other cells with which it is naturally present, but which lack the marker based on which the cells were isolated. For example, isolated tumor-initiating cell populations as disclosed herein are at least about 90%, or at least about 95%, free of non-tumorigenic cells. When referring to a tumor-initiating cell population that is described as a percentage purity, or a percentage free of non-tumorigenic cells, the cell stem cell subpopulation and total cancer cell population are typically quantified as live cells.

An enriched population of cells can be defined based upon the increased number of cells having a particular marker in a fractionated tumor-initiating cell population as compared with the number of cells having the marker in the non-fractionated cancer cell population. It may also be defined based upon tumorigenic function as the minimum number of cells that form tumors at limiting dilution frequency. An enriched tumor-initiating cell population can be enriched about 2-fold in the number of stem cells as compared to the non-fractionated tumor cell population, or enriched about 5-fold or more, such as enriched about 10-fold or more, or enriched about 25-fold or more, or enriched about 50-fold or more, or enriched about 100-fold or more. Enrichment can be measured with using any one of the tumor-initiating cell properties noted herein above, e.g., levels of marker expression or tumorigenicity.

The present invention provides methods for isolation of the disclosed tumor-initiating cell populations. For example, the method can comprise (a) providing dissociated tumor cells; (b) contacting the dissociated tumor cells with an agent that specifically binds to 5T4; (c) selecting cells that specifically bind to the agent of (b) at a level that is at least about 5-fold greater than cells that either do not express 5T4 or express 5T4 at a low level. The method can also comprise further selection based upon any of the positive or negative tumor-initiating cell markers disclosed herein or otherwise known in the art. When performing selection using a negative marker, e.g., excluding cells that express one or more negative markers, tumor-initiating cells may be identified as cells that show reduced expression of the marker as compared to differentiated cells or non-tumorigenic cells. Representative methods for isolation or enrichment of $5T4^{high}$, $CD24^{-/low}$, and/or $CD44^+$ tumor-initiating cell populations are described in Examples 1-4.

Tumor-initiating cells can be isolated or enriched by any suitable means known in the art, including FACS using a fluorochrome conjugated marker-binding reagent and primary culture using serum free conditions. Any other suitable method including attachment to and disattachment from solid phase, is also within the scope of the invention. Procedures for separation may include magnetic separation, using antibody-coated magnetic beads, affinity chromatography and panning with antibody attached to a solid matrix, e.g., a plate or other convenient support. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes that bind dead cells (such as propidium iodide (PI), or 7-AAD). Any technique may be employed that is not unduly detrimental to the viability of the selected cells.

I.B. Functional Properties of Tumor-Initiating Cells

As described herein, tumor-initiating cells of the invention are tumorigenic in vitro and in vivo, have characteristics of tumorigenic cells such as clonogenicity, and a highly proliferative nature. Subpopulations of lung tumor cell lines were identified that express $5T4^{high}$, $CD44^+$, and/or $CD24^{-/low}$ and that are significantly enriched for colony formation and proliferation. See Examples 1-4. The injection of tumor-initiating cells into a host animal consistently results in the successful establishment of tumors more than 75% of the time, such as more than 80% of the time, or more than 85%, or more than 90%, or more than 95% of the time, or 100% of the time.

Cancer stem cells of the invention give rise to tumors with the same differentiation state of the tumor of origin. For example, tumor-initiating cells isolated from poorly and moderately differentiated tumors give rise to poorly and moderately differentiated tumors in vivo, respectively. The molecular profile of the resultant tumors is also similar to the tumor of origin, notwithstanding the prior selection of tumor-initiating cells. Thus, the tumor-initiating cells show a capacity to differentiate or give rise to non-tumorigenic cells that make up the majority of mature cancer populations.

The tumor-initiating cells of the invention have a capacity for self-renewal, as demonstrated by the ability of $5T4^{high}$ and/or $CD24^{-/low}CD44^+$ cells but not $5T4^{low}$ and/or $CD24^{+/high}CD44^+$ cells to form tumors consistently. This feature allows tumor-initiating cells to retain multipotency and high proliferative potential throughout repeated cell divisions.

The tumor-initiating cells of the invention have a capacity for migration, as demonstrated by the ability of $5T4^{high}$ and/or $CD24^{-/low}CD44^+$ cells to migrate. In a transwell assay, $5T4^{high}$ and/or $CD24^{-/low}CD44^+$ cells migrated in a serum-dependent manner more efficiently than $5T4^{low}$ and/or $CD24^{+/high}CD44^+$ cells. In another assay, spheroids of $5T4^{high}$ and/or $CD24^{-/low}CD44^+$ cells migrated across fibronectin coated slides, but no little or migration of cells in $5T4^{low}$ and/or $CD24^{+/high}CD44^+$ cells spheroids was observed after twenty-four hours.

II. Applications

The tumor-initiating cell populations disclosed herein are useful for studying the effects of therapeutic agents on tumor growth, relapse, and metastasis. When isolated from a cancer patient, the efficacy of particular therapies can be tested and/or predicted based upon the unique genetic and molecular profile of the isolated population. Thus, the disclosed tumor-initiating cell populations provide means for developing personalized cancer therapies.

In one aspect of the invention, the genetic and molecular features of tumor-initiating cells are described to identify target molecules and/or signaling pathways. Accordingly, the present invention also provides arrays or microarrays containing a solid phase, e.g., a surface, to which are bound, either directly or indirectly, tumor-initiating cells (enriched populations of or isolated), polynucleotides extracted from tumor-initiating cells, or proteins extracted from the tumor-initiating cells. Monoclonal and polyclonal antibodies that are raised against the disclosed tumor-initiating cell populations may be generated using standard techniques. The identification of tumor-initiating cell target molecules, and agents that specifically bind tumor-initiating cells, will complement and improve current strategies that target the majority non-tumorigenic cells.

Microarrays of genomic DNA from tumor-initiating cells can also be probed for single nucleotide polymorphisms (SNP) to localize the sites of genetic mutations that cause cells to become precancerous or tumorigenic. The genetic and/or molecular profile of tumor-initiating cells may also be used in patient prognosis. See e.g., Glinsky et al., *J. Clin. Invest.*, 2005, 115(6): 1503-1521, which describes a death-from-cancer signature predictive of therapy failure.

In another aspect of the invention, the efficacy of cancer drugs or candidate cancer drugs can be tested by contacting isolated tumor-initiating cells with a test compound and then assaying for a change in tumor-initiating cell properties as described herein. For example, therapeutic compositions can be applied to tumor-initiating cells in culture at varying dosages, and the response of these cells is monitored for various time periods. Physical characteristics of these cells can be analyzed by observing cells by microscopy Induced or otherwise altered expression of nucleic acids and proteins can be assessed as is known in the art, for example, using hybridization techniques and Polymerase Chain Reaction (PCR) amplification to assay levels of nucleic acids, immunohistochemistry, enzymatic assays, receptor binding assays, enzyme-linked immunosorbant assays (ELISA), electrophoretic analysis, analysis with high performance liquid chromatography (HPLC), Western blots, radioimmunoassays (RIA), fluorescence activated cell sorting (FACs), etc.

The ability of therapeutic compounds to inhibit or decrease the tumorigenic potential of tumor-initiating cells can be tested by contacting tumor-initiating cells and a test compound, allowing a sufficient temporal period for response, and then assessing tumor-initiating cell growth in vitro. Following exposure to the test compound, the tumor-initiating cells can alternatively be transplanted into a host animal (i.e., preparation of a xenograft model, which is then monitored for tumor growth, cancer cell apoptosis, animal survival, etc.). In yet another screening format, test compounds are administered to a xenograft host animal (i.e., an animal bearing tumor-initiating cells and/or a resultant tumor). Additional phenotypes that may be assayed include cell viability, proliferation rate, regenerative capacity, and cell cycle distribution of tumor-initiating cells or resultant non-tumorigenic cancer cells, or any other phenotype relevant to therapeutic outcome.

Test compounds include known drugs and candidate drugs, for example, viruses, proteins, peptides, amino acids, lipids, carbohydrates, nucleic acids, antibodies, prodrugs, small molecules (e.g., chemical compounds), or any other substance that may have an effect on tumor cells whether such effect is harmful, beneficial, or otherwise. Test compounds include but are not limited to 2 2' 2"-trichlorotriethylamine, 2-ethylhydrazide, 2-pyrrolino-doxorubicin, 5-FU (5-fluorouracil), 6-azauridine, 6-diazo-5-oxo-L-norieucine, 6-mercaptopurine, 6-thioguanine, a camptothecin, a sarcodictyin, ABRAXANE®, ABT-510 (Abbott Labs), aceglatone, acetogenins, aclacinomysins, actinomycin, ADRIAMYCIN®, AG1478, AG1571 (SU 5271; Sugen), aidophosphamide glycoside, altretamine, aminoglutethimide, aminolevulinic acid, aminopterin, amsacrine, ancitabine, androgens, Angiostatin (EntreMed), Angizyme (AstraZeneca), anguidine, anti-metabolites, arabinoside ("Ara-C"), authramycin, azacitidine, azaserine, aziridines, benzodopa, bestrabucil, bevacizumab, bevacizumab (AVASTIN® Genentech), bexarotene, bisantrene, bleomycin, BMS-275291 (Bristol Myers Squib), Bortezomib (VELCADE® Millenium Pharm.), bryostatin, busulfan, cactinomycin, callystatin, calusterone, capecitabine, carabicin, carboplatin, carboquone, carminomycin, carmofur, carmustine, carzinophilin, CC-1065, chlorambucii, chioranbucil, chlornaphazine, chlorozotocin, cholophosphamide, chromomycinis, cisplatin, Combrestatin (Oxigene), CPT-11, cryptophycins, cyanomorpholino-doxorubicin, cyclooxygenase-2 (COX-2) inhibitors exisulind, cyclophosphamide, cyclosphosphamide, cytarabine, CYTOXAN®, dacarbazine, dactinomycin, daunomycin, daunorubicin, defofamine, demecolcine, deoxydoxorubicin, detorubicih, diaziquone, dideoxyuridine, difluorometlhylomithine (DMFO), docetaxel, dolastatin, doxifiuridine, doxorubicin, dromostanoione propionate, duocarmycin, edatraxate, edatrexate, eleutherobin, elformithine, elliptinium acetate, enediyne antibiotics, eniluracil, enocitabine, epirubicin, epitiostanol, erlotinib (tarceva), Erlotinib (TARCEVA® Genentech/OSI Pharm.), esorubicin, estramustine, ethylenimines, etoglucid, etoposide, etoposide (VP-16), floxuridine, fludarabine, folic acid analogues such as denopterin, folic acid replenisher such as frolinic acid, fotemustine, France), Fulvestrant (FASLODEX® AstraZeneca), gacytosine, gallium nitrate, Gefitinib (IRESSA® AstraZeneca), GEMZAR® (gemcitabine), hydroxyurea, ibandronate, idarubicin, ifosfamide, Imatinib mesylate (GLEEVEC® Novartis), improsulfan and piposuifan, irinotecan, Lapatinib (GSK572016, lentinan, Letrozole (FEMARA® Novartis), Leucovorin, lomustine, Lonafarnib (SCH 66336), lonidainine, losoxantrone, mannomustine, marcellomycin, marimastate (British Biotech), maytansinoids such as maytansine and ansamitocins, mechlorethamine, mechlorethamine oxide hydrochloride, melphalan mepitiostane, mercaptopurine, methotrexate, methotrexate and 5-fluorouracil (5-FU), rnethylamelamines, meturedopa, mitobronitol, mitoguazone, mitolactol, mitomycin C, mitornycins, mitotane, mitoxantrone, mopidanmol, morpholino-doxorubicin, mycophenolic acid, MYLOTARG® (gemtuzumab ozogamicin, Wyeth), NAVELBINE® (vinorelbine), Neovastat (Aeterna Zentaris), nimustine, nitraerine, nitrogen mustards, nogalamycin, novantrone, novembichin, olivomycins, or vinorelbine, ELOXATIN® (Oxaliplatin Sanofi), paclitaxel, pancratistatin, pemetrexed disodium (ALIMTA®, pentostatin, peplomycin, phenamet, phenesterine, pipobroman, pirarubicin, podophyllinic acid, potfiromycin, prednimustine, procarbazine; proteasome inhibitors, pteropterin, PTK787/ZK 222584 (Novartis), puromycin, quelamycin, ranimnustine, Rapamycin (Sirolimus, RAPAMUNE®, Wyeth), razoxane, retinoic acid, retinoids, rhizoxin, rodorubicin, roridin A, sizofuran, Sorafenib (BAY43 9006, Bayer), spirogermanium, spongistatin, streptonigrin, streptozocin. SU5416, SU6668 (Sugen), Sunitinib (Pfizer), SUTENT® (SU11248 Pfizer), T-2 toxin, TAXOL® (paclitaxel; Bristol-Myers Squibb). TAXOTERE® (docetaxel; Rhone-Poulenc Rorer), temsirolimus (TORISEL®, Wyeth), teniposide, tenuazonic acid, testolactone; anti-adrenals, thalidomide (Celgene), thiamiprine, thioguanine, thiotepa, topoisomerase inhibitor RFS 2000, topotecan, triaziquone, trichothecenes, triethylenemelamine, triethylenephosphoramide, triethylenethiophosphoramide, trilostane, trimethylomelamine, trimetrexate, trofosfamide, tubercidin, ubenimex, uracil mustard, uredopa, urethane, vaccines. VEGF-Trap (Regeneron Pharm), verracurin A, vinblastine, vincristine, vindesine, vinorelbine, Vitaxin II (Medimmune) and Cilengitide (Merck KgaA), xeloda, ZD6474 (ZACTIMA® AstraZeneca), zinostatin, zorubicin and pharmaceutically acceptable salts, acids derivatives and antibody conjugates of any of the above.

For use in any of the above-noted applications, or other applications, tumor-initiating cells of the invention may be cryopreserved until needed for use. For example, the cells can be suspended in an isotonic solution, preferably a cell culture medium, containing a particular cryopreservant. Such cryopreservants include dimethyl sulfoxide (DMSO), glycerol and the like. These cryopreservants are used at a concentration of 5-15%, such as 8-10% Cells are frozen gradually to a temperature of $-10°$ C. to $-150°$ C. such as $-20°$ C. to $-100°$ C., or at $-150°$ C.

EXAMPLES

The following examples have been included to illustrate modes of the invention. Certain aspects of the following examples are described in terms of techniques and procedures found or contemplated by the present co-inventors to work well in the practice of the invention. These examples illustrate standard laboratory practices of the co-inventors. In light of the present disclosure and the general level of skill in the art, those of skill will appreciate that the following examples are intended to be exemplary only and that numerous changes, modifications, and alterations may be employed without departing from the scope of the invention.

Example 1

Isolation of $CD24^{-/low}CD44^+$ Tumor Initiating Cells Using Non Small Cell Lung Cancer Cell Lines H460 cells were obtained from the American Type Culture Collection (ATCC) in Manassas, Va., United States of America. The H460 cell line was derived from the pleural fluid of a patient with large cell cancer of the lung (Gazdar et al., *Science*, 1989, 246: 491494). HCC2429 cells were obtained from J. Minna. See Haruki et al., *J. Med. Genet.*, 2005, 42(7):558-64. All experiments with H460T cells were performed with cells between passage numbers 37-51, because these cells were observed to have more robust phenotypes than lower passage cells. Higher-passage cells are referred to as H460T to distinguish them from the low-passage H460 that were originally obtained from ATCC. All cells were incubated at 37° Celsius with 5.0% carbon dioxide ($CO_2$). H460T cells were cultured in RPMI-1640 (GIBCO®, available from Invitrogen of Carlsbad, Calif., USA). See Moore et al., *JAMA*, 1967, 199: 519-524, 10% fetal bovine serum (FBS, GIBCO®, available from Invitrogen of Carlsbad, Calif., USA), 2 mM additional glutamine, 100 IU/ml penicillin, 100 μg/ml streptomycin, 1 mM sodium pyruvate, 0.1% sodium bicarbonate, 045% additional glucose, and 10 mM 4-(2-hydroxyethyl)-1-piperazineethanesulfonic acid (HEPES). HCC2429 cells were cultured in RPMI-1640, 10% FBS, 2 mM additional glutamine, 100 IU/ml penicillin, 100 μg/ml streptomycin. Karyotyping and short tandem repeat (STR) analysis of H460T confirmed its H460 origin, however the Y chromosome was absent in H460T cells and present in most H460 cells.

For flow cytometry analysis, cells were harvested with GIBCO® TRYPLE™, washed in Hanks Balanced Salt Solution without calcium and magnesium (HBSS) with 3% heat-inactivated calf serum (HICS), incubated with 100 μg/ml DNase, 5 mM $MgCl_2$ and 50 μg/ml human immunoglobulin (IgG), incubated with antibodies or isotype controls, washed, and resuspended in HBSS with 3% HICS, 25 μg/ml DNase, 1 mM $MgCl_2$, and 25 mM HEPES. Xenografts were minced to a paste-like consistency, incubated in Collagenase/Hyaluronidase (Stem Cell Technologies of Vancouver, British Columbia, Canada) for 1 hour with frequent mixing in a 37° C. water bath, and filtered through a 40-micron filter. The cell suspension was treated with Red Blood Cell Lysis Buffer (Roche Diagnostics Corporation of Indianapolis, Ind., USA) followed by ACCU-PREP® (Axis of Oslo, Norway), both according to manufacturer's instructions. Anti-human CD24 (#555428) and CD44 (#559942) monoclonal antibodies were obtained from BD Biosciences of San Jose, Calif., USA). Anti-5T4 antibody clone H8 (Hole & Stern, *Br. J. Cancer*, 1988, 57(3): 239-46) was obtained from Oxford Biomedica of Oxford, United Kingdom.

Figure 1B:
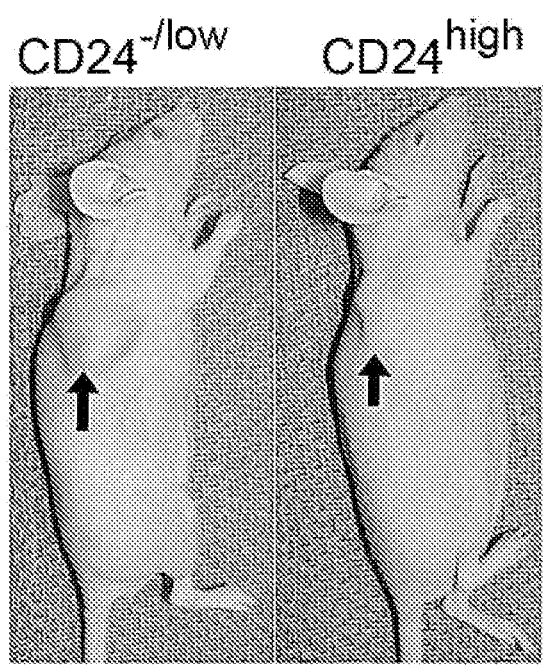
Figure 1C:
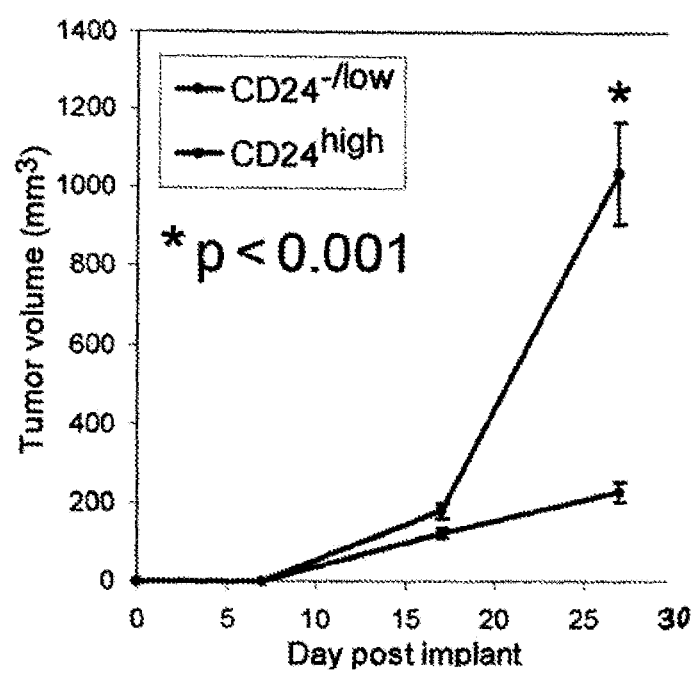
Figure 1D:
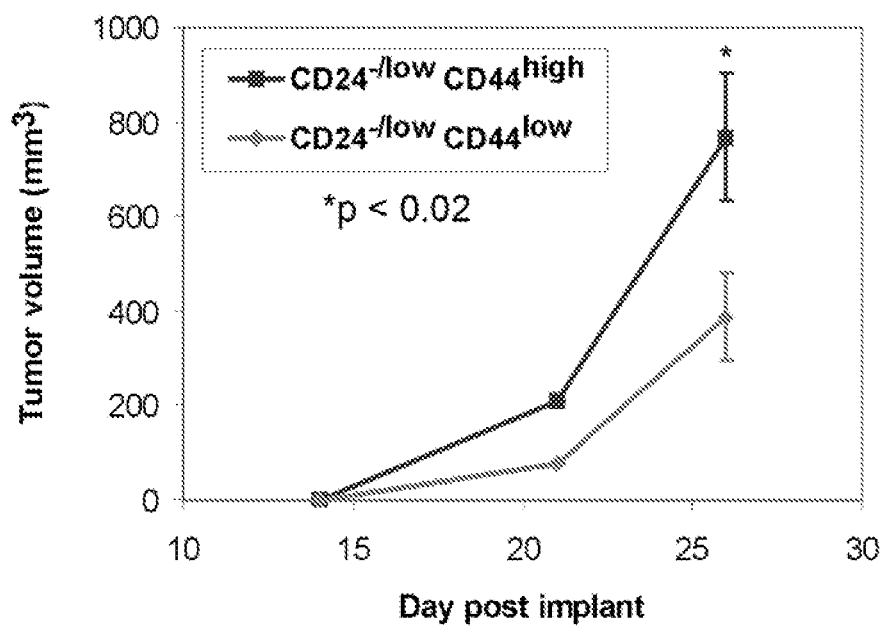

Labeling the H460T NSCLC cell line with anti-CD24 and anti-CD44 antibodies revealed distinct populations with a stable distribution over long periods in culture (FIG. 1A). When these populations were separated by fluorescence-activated cell sorting and implanted subcutaneously into immunocompromised nu/nu mice, the $CD24^{-/low}CD44^+$ cells formed large tumors rapidly, whereas the $CD24^{high}CD44^+$ cells slowly formed small tumors ($p<0.001$; FIGS. 1B-1C), $CD24^{-/low}CD44^+$ cells also formed larger tumors than the third population, $CD24^{-/low}CD44^{low}$ ($p<0.02$; FIG. 1D). These studies demonstrated that $CD24^{-/low}$ and $CD44^+$ enrich for tumorigenic potential in H460T.

Figure 1E:
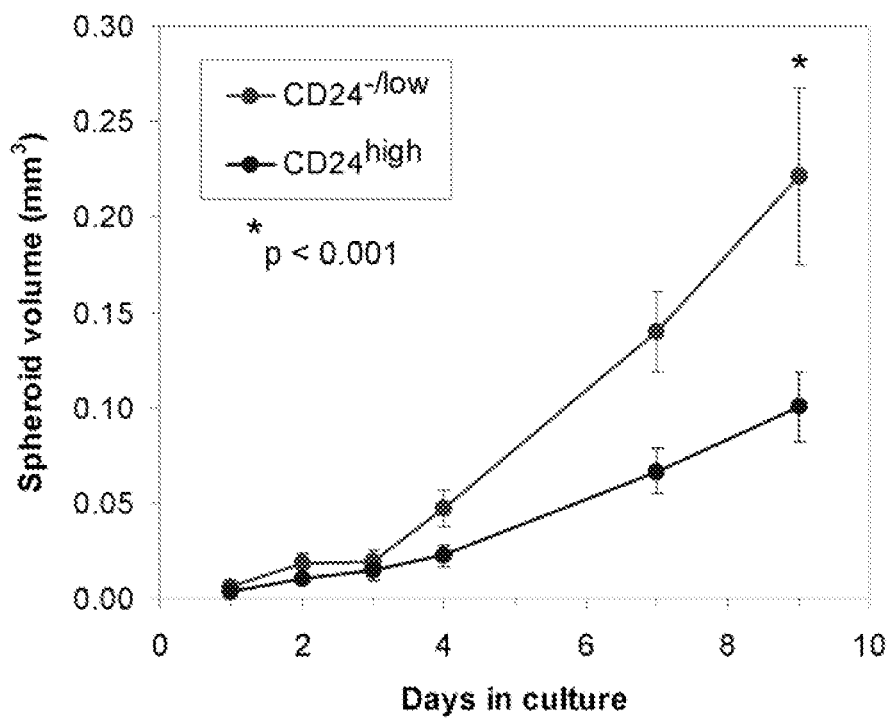

The $CD24^{-/low}CD44^+$ cells were phenotypically distinct from the $CD24^{high}CD44^+$ cells in several additional assays. First, the $CD24^{-/low}CD44^+$ cells grew more rapidly than the $CD24^{high}CD44^+$ cells in three-dimensional culture as spheroids ($p<0.001$; FIG. 1E). No difference in proliferation rate, cell cycle profile, or cell size was detected between the populations in two-dimensional culture.

Figure 1F:
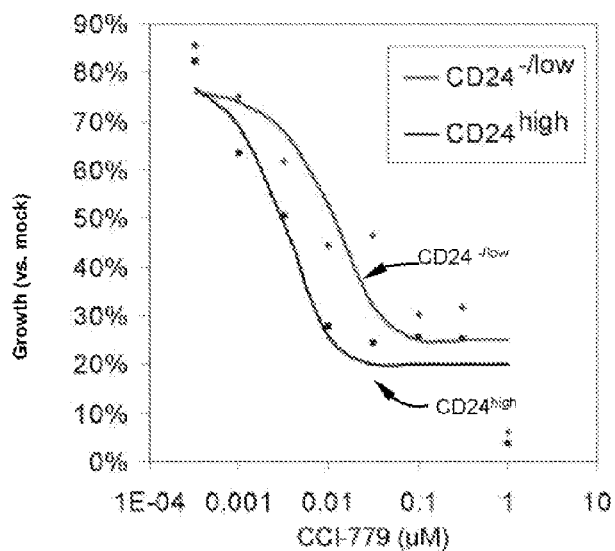

Second, the populations exhibited a differential response to the mTOR inhibitor CCI-779, a rapamycin analog that was recently approved for treatment of advanced renal cell carcinoma (Faivre et al., *Nat. Rev. Drug Discov.*, 2006, 5: 671-688). The $CD24^{-/low}CD44^+$ cells were 5- to 10-fold more resistant to CCI-779 than $CD24^{high}CD44^+$ cells (FIG. 1F). In contrast, the populations responded equally to camptothecin, 5-fluoruracil, and ionizing radiation, indicating that the differential response to CCI-779 was specific.

Figure 1G:
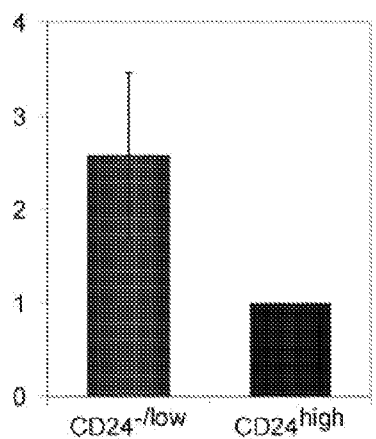
Figure 1H:
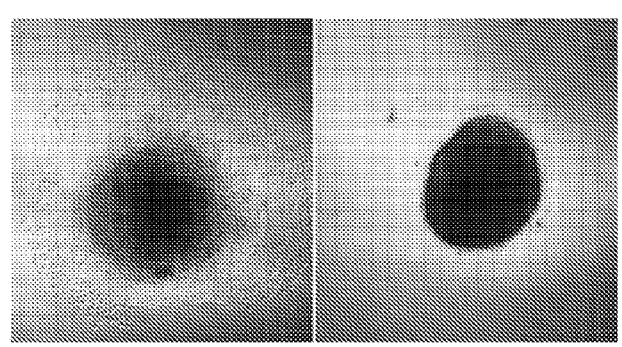

Third, $CD24^{-/low}CD44^+$ cells migrated more efficiently than $CD24^{high}CD44^+$ cells, as shown using a transwell migration assay and a spheroid growth assay. To perform a transwell migration assay, sorted cells that were cultured overnight in growth medium and then serum-starved for 24 hours. 500,000 cells per well were plated in serum-free media in 8.0-micron pore 24 mm-diameter transwells. Media with or without serum was added to the outer chamber and cells were incubated for 16-18 hours. Cells were fixed with formaldehyde and stained with crystal violet. Cells were carefully scraped from the inner chamber with wet and dry Q-tips such that cells that had migrated to the outer chamber could be counted under the microscope. Eight to ten fields per well were counted. Using this assay, $CD24^{-/low}CD44^+$ cells migrated 2.5-fold more efficiently than $CD24^{high}CD44^+$ cells in a serum-dependent manner (n=4; FIG. 1G). To perform a spheroid growth assay, 100,000 sorted cells in 5 ml of culture medium were seeded on 60 mm polystyrene cell culture dishes previously coated with 5 ml of tissue culture grade agar (0.7%) in culture medium. The dishes were incubated for 5 days at 37° C. Spheroids with a diameter of 0.2 mm were selected and placed on fibronectin-coated slides (BD Biosciences). Migration of cells in $CD24^{-/low}CD44^+$ spheroids across the fibronectin-coated slides was evident after 24 hours and at subsequent timepoints, but little or no migration of cells in $CD24^{high}CD44^+$ spheroids was observed (FIG. 1H). There was no difference in growth rate of the spheroids over the 3-day period of this experiment.

Figure 2A:
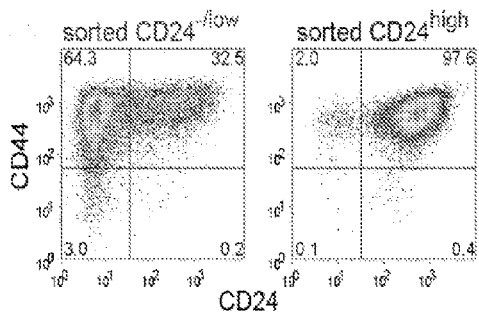
FIGS. 2A-2E show the multipotency of $CD24^{-/low}CD44^+$ cells in H460T. $CD24^{-/low}CD44^+$ cells are labeled "$CD24^{-/low}$" and $CD24^{high}CD44^+$ cells are labeled "$CD24^{high}$".
Figure 2B:
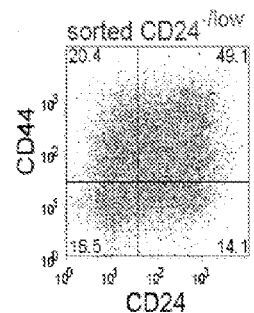
Figure 3A:
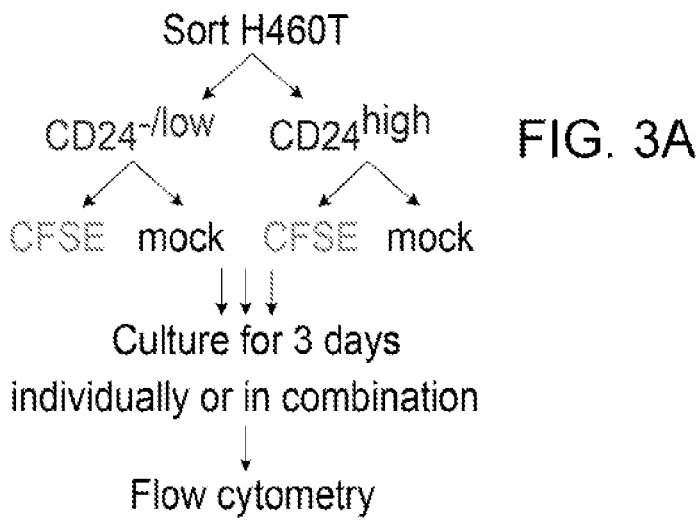
FIGS. 3A-3C show the multipotency of H460T cells sorted based upon CD24 expression.
Figure 3B:
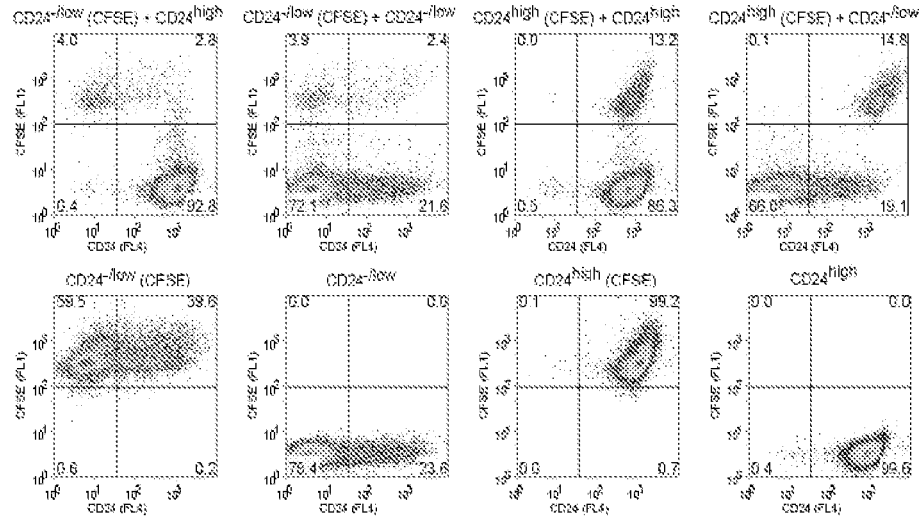
Figure 3C:
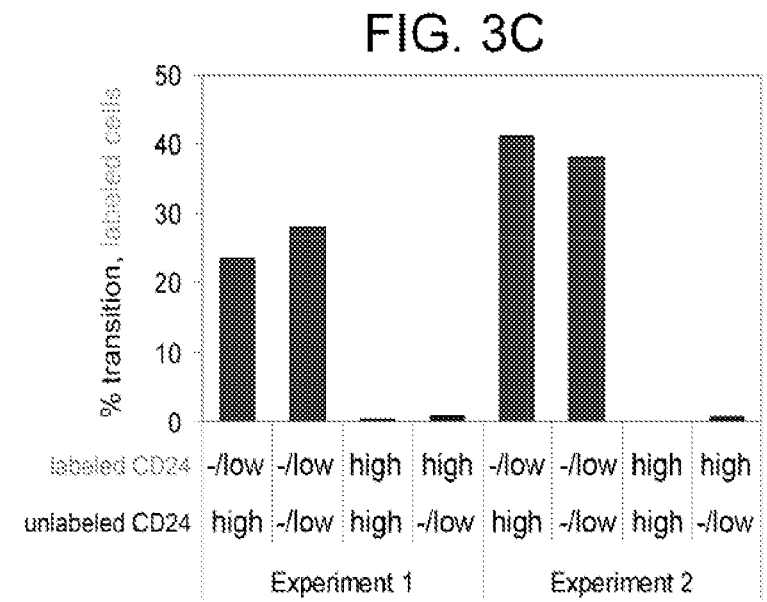

To determine whether the tumor-initiating population of H460T also possessed stem cell-like characteristics, sorted cells were maintained in culture and monitored regularly by flow cytometry. $CD24^{-/low}CD44^+$ cells always gave rise to a significant population of $CD24^{high}CD44^+$ cells evident as early as three days after the sort (FIG. 2A). In contrast, $CD24^{high}CD44^+$ cells remained $CD24^{high}CD44^+$ through the latest time point of two months post-sort (FIG. 2A). These results indicated a multipotency phenotype of the tumor-initiating cells. To determine whether the observed transition occurs in the context of the parental line, labeled and unlabeled populations were co-cultured. When co-cultured with $CD24^{high}CD44^+$ cells, $CD24^{-/low}CD44^+$ cells were also multipotent (FIGS. 3A-3C), which implied that the mutlipotency phenotype exists in culture of parental H460T. Multipotency was also observed in vivo: xenografts grown from $CD24^{-/low}CD44^+$ cells typically contained ~50% $CD24^{high}$ cells (FIG. 2B).

Figure 2C:
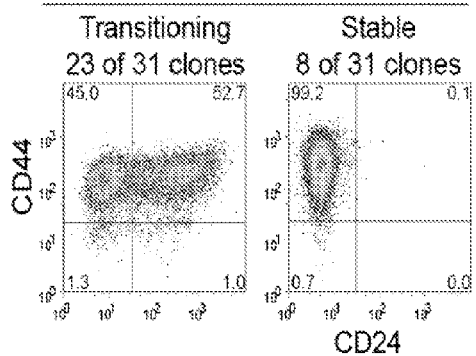
Figure 2D:
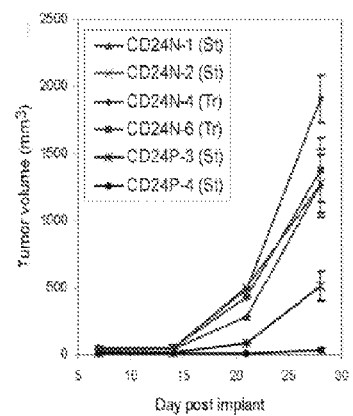

Clonal analysis was performed to verify that the multipotency could be followed at the single cell level. Colonies from single $CD24^{-/low}CD44^+$ or $CD24^{high}CD44^+$ cells were expanded into clonal lines. Most (23/31) of the $CD24^{-/low}CD44^+$ derived clonal lines contained >10% $CD24^{high}$ cells ("transitioning clones"), but some (8/31) contained <1% $CD24^{high}$ cells ("stable clones"). All (6/6) $CD24^{high}CD44^+$ derived clonal lines contained 100% $CD24^{high}$ cells (FIG. 2C). Consistent with the above results from the sorted parental line, sorted $CD24^{-/low}CD44^+$ cells from all tested $CD24^{-/low}CD44^+$ clonal lines were highly tumorigenic, while sorted $CD24^{high}CD44^+$ cells from all tested $CD24^{high}CD44^+$ clonal lines formed small or no tumors (FIG. 2D).

Figure 2E:
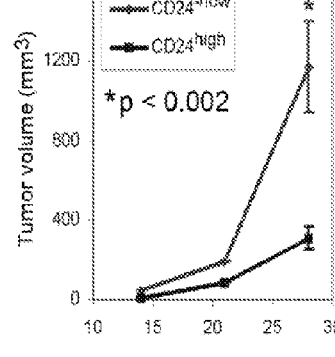
Figure 2E:
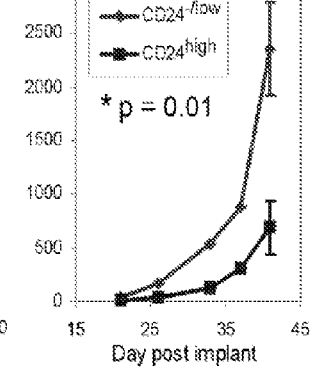
Figure 2E:
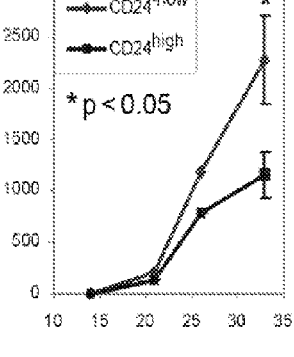

To test whether $CD24^{high}CD44^+$ cells show reduced tumorigenic potential as compared to $CD24^{-/low}CD44^+$ cells, transitioning $CD24^{-/low}CD44^+$ clonal lines were sorted into $CD24^{-/low}CD44^+$ and $CD24^{high}CD44^+$ cells, and the sorted cells were implanted into animals. In three clonal lines, the CD24$^{-/low}$CD44$^+$ cells formed larger tumors than the CD24$^{high}$CD44$^+$ cells (p<0.005 in clone 24N-4; p=0.01 in clone 24N-10; p<0.05 in clone 24N-25; FIG. 2E). No significant difference was observed in three other clonal lines. Thus CD24$^{-/low}$CD44$^+$ cells from H460T can give rise to less tumorigenic, functionally distinct CD24$^{high}$CD44$^+$ cells. These results demonstrate the existence of multipotent tumor-initiating cells in H460T.

Figure 4A:
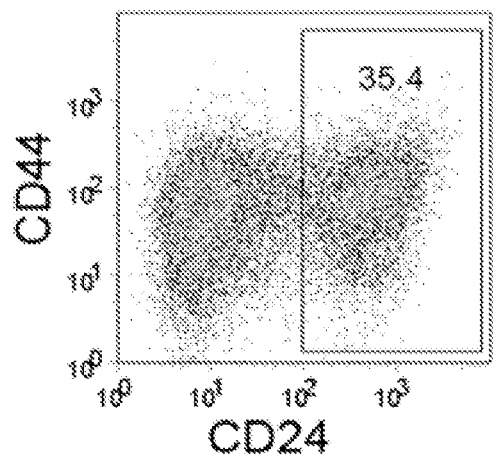
FIGS. 4A-4C show $CD24^{-/low}$ identifies tumor-initiating cells in cultured HCC2429 cells.
Figure 4B:
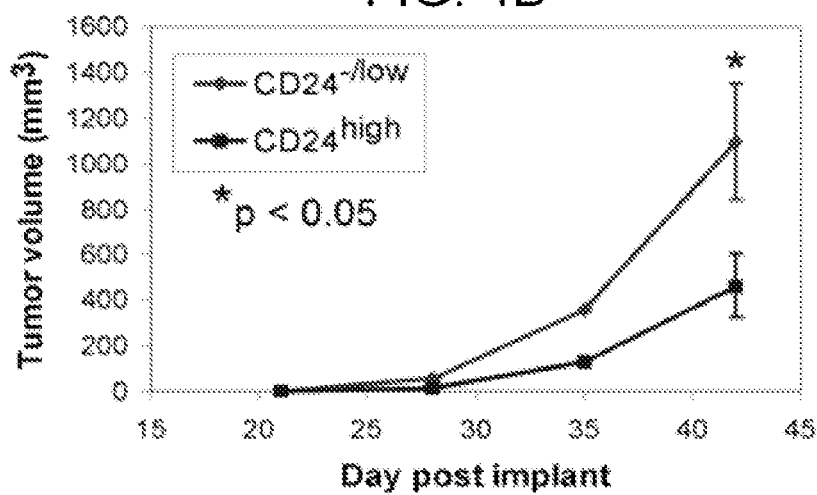
Figure 4C:
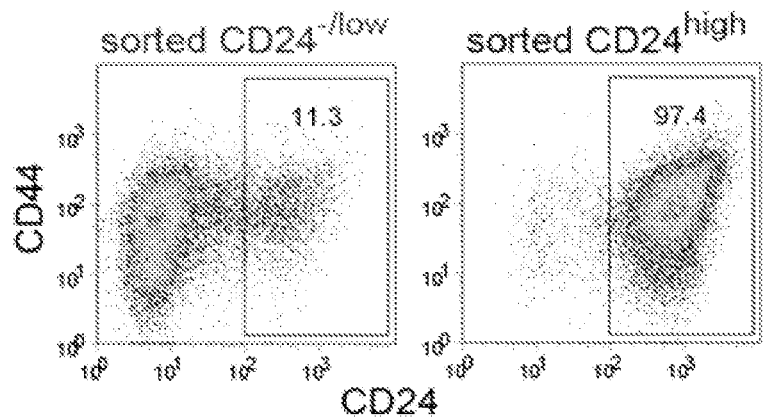

Other NSCLC cell lines were assessed for heterogeneity with respect to CD24 and CD44. The HCC2429 line (Dang et al., *J. Natl. Cancer Inst.*, 2000, 92, 1355-1357) contained two distinct CD24 populations, CD24$^{-/low}$ and CD24$^{high}$ (FIG. 4A). FACS-isolated CD24$^{-/low}$ cells formed significantly larger tumors than CD24$^{high}$ cells (p<0.05: FIG. 4B). In addition, CD24$^{-/low}$ cells gave rise to CD24$^{high}$ cells in culture, whereas CD24$^{high}$ cells remained CD24$^{high}$ (FIG. 4C).

Example 2

Figure 5:
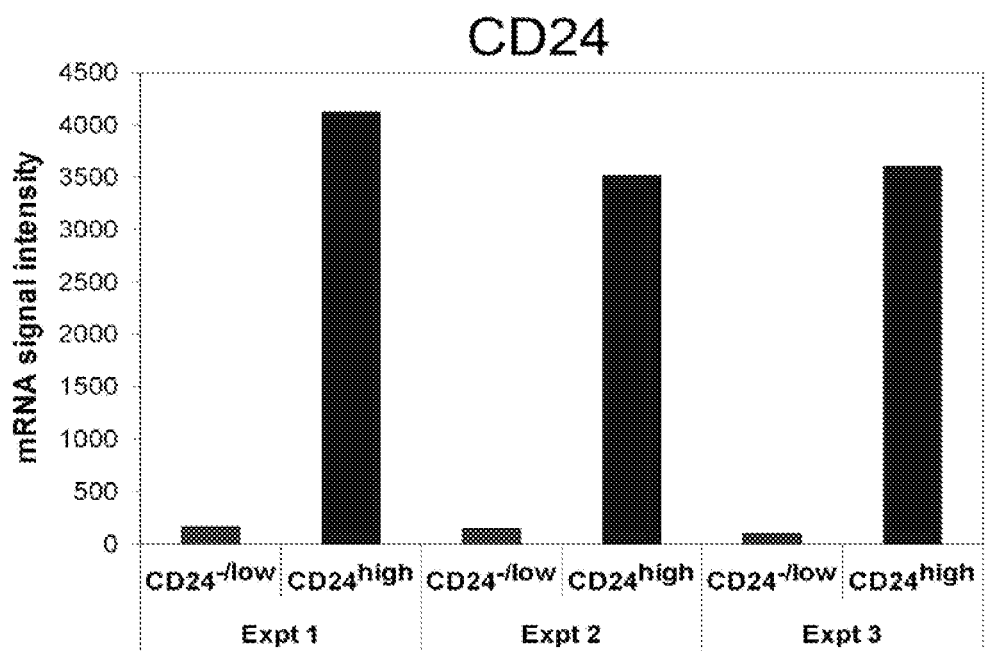
FIG. 5 is a bar graph showing CD24 mRNA levels on Affymetrix GENECHIP® oligonucleotide arrays hybridized with triplicate samples of mRNA transcripts prepared from $CD24^{-/low}CD44^+$ and $CD24^{high}CD44^+$ cells.
Figure 6A:
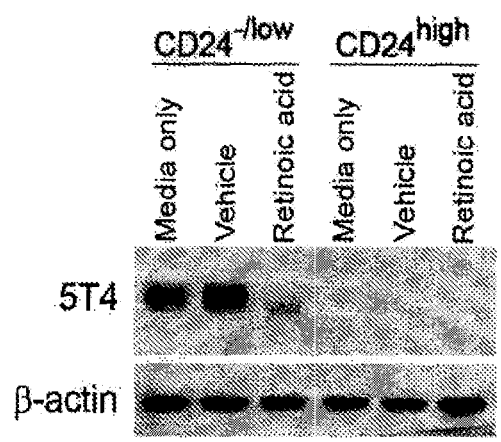
FIGS. 6A-6B show that the oncofetal protein 5T4 (TPBG) is expressed in H460T multipotent tumor-initiating cells.

Identification of 5T4$^+$ Tumor Initiating Cells in Non Small Cell Lung Cancer Cell Lines To identify genes that might underlie the phenotypic differences between CD24$^{-/low}$CD44$^+$ and CD24$^{high}$CD44$^+$ cells, gene expression profiles were generated from triplicate samples of FACS-isolated populations. As expected, the mRNA levels of CD24 were consistently high in CD24$^{high}$CD44$^+$ cells and low in CD24$^{-/low}$CD44$^+$ cells (FIG. 5). Levels of 5T4 (also known as TPBG) were 4.5-fold higher in CD24$^{-/low}$CD44$^+$ cells compared to CD24$^{high}$CD44$^+$ cells (FIG. 6A).

Figure 6B:
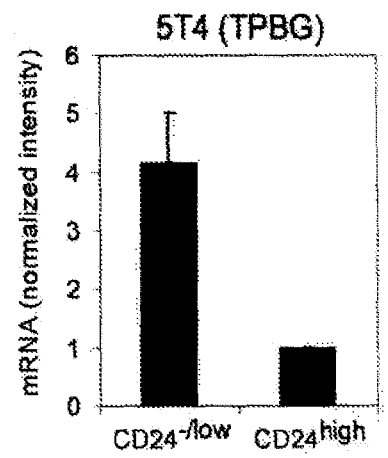

To determine 5T4 expression under conditions of growth and differentiation, cells were harvested at several time points, and protein extracts were subjected to immunoblot analysis. Cells were washed with PBS and lysed in 0.5% v/v NP40 in 25 mM Tris-buffered saline pH 7.4 (TBS). After protein estimation (MICROBCA™ Protein Assay Kit, Pierce of Rockford, Ill., USA), the lysates were mixed with non-reducing Laemmli sample buffer (Biorad of Hercules, Calif., USA) and 10 µg samples were loaded in each well of a non-reducing 4-20% polyacrylamide gradient gel (NOVEX®, available from Invitrogen of Carlsbad, Calif., USA). The samples were run for two to three hours at 125 volts and transferred to a PVDF (polyvinylidene fluoride) membrane by means of a Novex® electrophoresis transfer system. The membrane was blocked overnight with 5% milk in Tris-buffered saline Tween-20 (TBST) with 1% goat serum, probed with anti-5T4 antibody H8 at 1 µg/ml in 5% milk in TBST, washed and probed with HRP conjugated goat anti-muIgG at 1:5,000 dilution. The ECL detection system was used (Amersham of Burlington, Mass., USA). Immunoblot analysis with anti-5T4 antibody showed expression of 5T4 protein in CD24$^{-/low}$CD44$^+$ but not CD24$^{high}$CD44$^+$ cells (FIG. 6B).

Immunofluorescence of parental H460T with anti-5T4 and anti-CD24 antibodies demonstrated that 5T4 and CD24 stainings were exclusive and that nearly all of the CD24$^{-/low}$CD44$^+$ cells also expressed 5T4. 5T4 was expressed in all of the CD24$^{-/low}$CD44$^+$ clonal lines described in Example 1.

To further assess 5T4 expression in tumor cell lines, sorted cells were treated with all-trans retinoic acid to induce differentiation and then subjected to immunoblot analysis. Sorted cells were obtained by FACS and 2.3×10$^5$ cells of each immunophenotype were plated in 6-well dishes in complete growth medium. After 24 hours, medium was removed, cells were washed 2 times with PBS and re-fed with 0.5% FBS growth medium. Medium was removed 24 hours later and replaced with 0.5% FBS growth medium supplemented with vehicle control or 10 µM all-trans retinoic acid (Sigma of St. Louis, Mo., USA). Cells were cultured for 72 hours, washed in PBS and lysed directly in 1× Laemmli buffer (Bio-Rad of Hercules, Calif., USA) for anti-5T4 western blot analysis. 5T4 expression was dramatically reduced in the treated CD24$^{-/low}$CD44$^+$ cells (FIG. 6B), which indicated that 5T4 was associated with the undifferentiated state in cancer cells.

Example 3

A Differentiation Model for Tumor Initiating Cells in Non Small Cell Lung Cancer Primary Cultures Primary serum-free cultures were established from freshly resected NSCLC samples. The cells were cultured under conditions to promote self-renewal, or induced to differentiate by exposure to the air-liquid interface in the presence of retinoic acid. The air-liquid interface is considered to be a physiological environment for lung cells and has been used to study fetal lung development (Vaughan et al. *Differentiation*, 2006, 74: 141-148). To induce differentiation using this model, cultures were prepared and treated as follows. Millicell 1 µM PET hanging cell culture inserts (Millipore of Billerica, Mass., USA) were placed inside 6-well dishes. Membranes were pre-wet with phosphate buffered saline (PBS), 25×10$^5$ primary cells obtained from 87426A1 tumor tissue were plated onto each insert and filled with BEBM medium. After 1-2 days, medium was removed from upper and lower chambers, rinsed with PBS and CnT-23 medium containing 50 nM retinoic acid and 1 mM CaCl$_2$ (Millipore of Billerica, Mass., USA) was added back to lower chamber leaving cells in upper chamber exposed to the air. Lifted cultures were fed every 2 days with fresh medium or harvested at indicated time points in Buffer RLT (QIAGEN of Valencia, Calif., USA) for RNA isolation or TBS (Tris-buffered saline)/0.5% NP40 (Tergitol-type NP-40, Sigma-Aldrich of St. Louis, Mo., USA) for anti-5T4 Western blot analysis. For gene expression profiling, replicate growth samples were analyzed together, and due to limited sample, differentiation samples from days 8, 16, and 24 were pooled and analyzed together. Live cell imaging revealed that monolayer cultures efficiently formed 3D-stratified epithelium upon exposure to the air-liquid interface and 50 nM retinoic acid for 18 days (FIG. 7A).

To determine 5T4 expression under conditions of growth and differentiation, cells were harvested at several time-points, and protein extracts were subjected to immunoblot analysis as described in Example 2. 5T4 levels were high under growth conditions and decreased quickly and dramatically upon differentiation (FIG. 7B).

To obtain a global view of this differentiation model, the experiment was repeated and gene expression profiles were generated from cells under conditions of growth and differentiation. See Examples 5 and 6. Consistent with the above results, 5T4 expression decreased and CD24 expression increased during differentiation (FIG. 7C). The gene expression profiles of the primary culture in growth and differentiation were also compared to those of the H460T CD24$^{-/low}$CD44$^+$ and CD24$^{high}$CD44$^+$ populations (see Example 5). A significant fraction of the genes that were expressed at higher levels during differentiation of the primary culture were also expressed at higher levels in the CD24$^{high}$CD44$^+$ cells (FDR=0.0015). For statistical comparison of the H4601 and 87426 data sets, the top 250 upregulated genes in the differentiated 87426 culture were compared in the H460T populations. FIG. 7D shows the expression difference for genes that are above noise level in the H460T data set. Statistical analysis yielded the False Discovery Rate of 0.0015. This analysis indicates that these very different experimental systems are physiological models of the differentiation hierarchy in NSCLC. The microarray data were confirmed by flow cytometry (FIGS. 7E-7F).

Figure 7G:
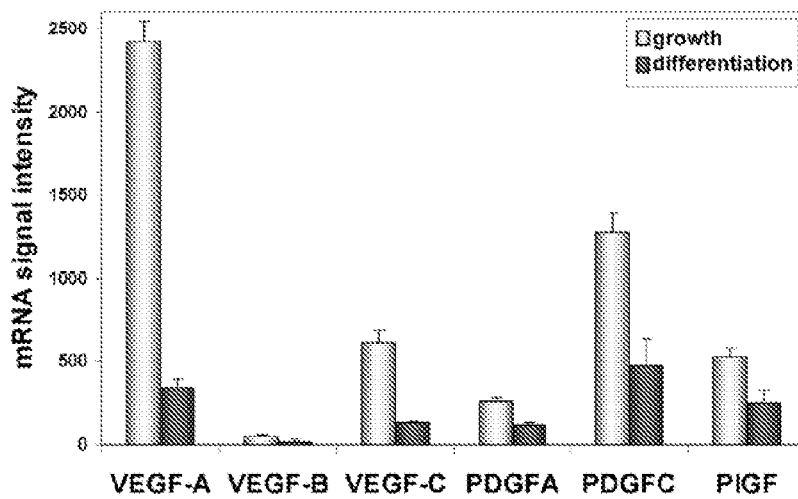

The expression profiles also revealed striking patterns of genes involved in epithelial-mesenchymal transition and angiogenesis. The epithelial-mesenchymal transition markers vimentin, fibronectin, Slug, and Twist were expressed at high levels under growth conditions compared to the differentiated state (FIG. 7C). In contrast, the epithelial markers mucin and several cytokeratins were expressed at high levels during differentiation compared to growth conditions (FIG. 7C). The angiogenesis factors VEGF-A, -B, -C, PDGF-A and -C, and PIGF, were expressed at significantly higher levels under growth conditions compared to differentiation (FIG. 7G).

An unbiased meta-analysis of the expression data revealed several gene signatures with significant expression changes during differentiation (Table 1). Gene sets with higher expression in undifferentiated cells included signatures of poor clinical prognosis, stem cells, oncogenic signaling, and developmental signaling. Gene sets with higher expression in differentiated cells included signatures of better clinical prognosis, differentiated tumors, and differentiated cells. Information from the Broad Institute's Molecular Signatures Database used in this analysis is presented in Table 2, including a list of genes (members) for each of the gene sets identified in Table 1. All NTk's in Table 1 have a false discovery rate (FDR)<=0.01. NTk>0 indicates direct correspondence with differentiated primary culture. NTk<0 indicates inverse correspondence with differentiated primary culture.

Lengthy table referenced here

US09340774-20160517-T00001

Please refer to the end of the specification for access instructions.

Lengthy table referenced here

US09340774-20160517-T00002

Please refer to the end of the specification for access instructions.

Taken together, the foregoing results define a differentiation hierarchy in a primary NSCLC culture and indicate that retinoic acid differentiation can partially reverse the tumorigenic profile.

Example 4

Identification of Tumor Initiating Cells in Non Small Cell Lung Cancer Cell Xenografts Primary xenograft lines were prepared using female, athymic nu/nu (nude) and NOD-SCID mice (18-23 g) obtained from Charles River of Wilmington, Mass., USA. To assess tumorigenic potential of sorted cells, the cells were implanted in 50% Matrigel (BD Biosciences) subcutaneously between the shoulder blades. Typically, for H460T and HCC2429, 100 sorted cells were implanted per nude mouse. For the 37622 line, 2500 cells were implanted per nude mouse. For the 60257 line, 5000 cells were implanted per nod-scid mouse. Tumors were measured at least once a week with tumor volume=$0.5 \times (\text{tumor width}^2) \times (\text{tumor length})$. Each implant line was propagated by explanting a fragment of the resulting xenograft into new animals and thus was maintained exclusively in vivo. In each line, the histology of the xenografts resembled that of the original tumor. Samples were cryopreserved so that experiments could be performed and repeated in low-passage xenografts.

Immunohistochemical analysis of primary implants was performed using standard techniques and revealed heterogeneous expression of 5T4. In multiple implant lines the highest 5T4 expression was observed at the tumor-stroma interface. In xenografts prepared using 37622 cells, a similar staining pattern was observed for vimentin, a marker of the epithelial-mesenchymal transition of differentiation. Vimentin was not detected in xenografts prepared using 60274 cells.

Figures 8A, 8B:
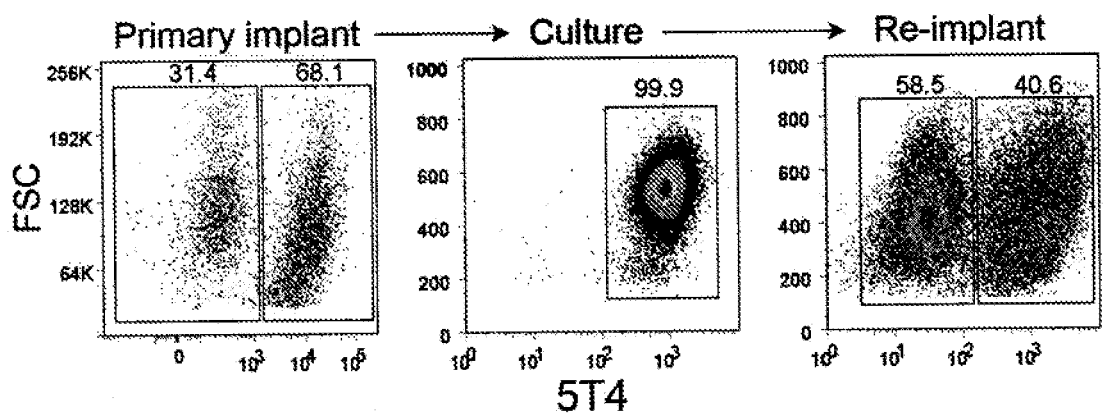
FIGS. 8A-8B show heterogeneous 5T4 expression in NSCLC primary implant xenografts.

Heterogeneous 5T4 expression in xenografts was also observed by flow cytometry. Dissociated 37622 implants showed distinct $5T4^{high}$ and $5T4^{low}$ populations were evident among the viable human cells (FIG. 8A). When a serum-free culture was established from 37622 xenografts, all cells expressed high 5T4 (FIG. 8A), which was consistent with the culture conditions that promote stem cell growth. When these cells were re-implanted into animals, the resulting tumors were heterogeneous for 5T4 expression (FIG. 8A).

To determine whether 5T4 expression was associated with higher tumorigenicity, as in H460T, primary implant xenografts were dissociated and FACS-isolated cells were implanted into animals. $5T4^{high}$ cells were more tumorigenic than $5T4^{low}$ cells in 37622 and 60257 implant lines (FIG. 8B).

Example 5

Additional Biomarkers of Tumor Initiating Cells

Cells harvested from cultured cell lines (as described in Examples 1 and 2) were resuspended in lysis buffer (QIAGEN of Valencia, Calif., USA) and total RNA was purified using QIAGEN RNEASY® columns following the manufacturer's instructions. For xenograft tumors (as described in Example 4), tumor samples were first disrupted by sonication in 3 ml ice-cold 4 M guanidinium/10% sodium acetate buffer (RNAGENTS®, Promega of Madison, Wis., USA), extracted 2× with phenol-chloroform-isoamyl alcohol (50:48.2) and RNA precipitated from aqueous phase using an equal volume of isopropanol. The precipitate was subsequently resuspended in lysis buffer (QIAGEN) and total RNA purified using QIAGEN RNEASY® columns following the manufacturer's instructions.

cDNA was synthesized from 10 μg of total RNA using the SUPERSCRIPT® Kit (Gibco BRL of Gaithersburg, Md., USA) essentially as described by Byrne at al., in F. e. a. Ausubel, ed., *Current Protocols in Molecular Biology*, 2000, New York: John Wiley and Sons, Inc. First strand synthesis was carried out at 50° C. to prevent mispriming from ribosomal RNA and utilized a T7 RNA polymerase promoter containing poly-T primer (T7T24) for subsequent in vitro antisense RNA (cRNA) amplification and biotin labeling. cDNA was purified using GENECHIP® sample cleanup module (Affymetrix of Santa Clara Calif., USA) following the manufacturer's instructions. In vitro T7 polymerase driven transcription reactions for synthesis and biotin labeling of antisense cRNA utilized GENECHIP® Expression 3'-Amplification Reagent kit (Affymetrix of Santa Clara Calif., USA) following the manufacturer's instructions. Synthesized cRNA was purified using QIAGEN RNEASY® columns.

For each sample, 10 μg of biotin-labeled cRNA was fragmented and hybridized to Human Genome U133+2 GENECHIP® oligonucleotide arrays (Affymetrix of Santa Clara, Calif., USA) using buffers and conditions recommended by manufacturer. GENECHIP® oligonucleotide arrays were washed and stained with Streptavidin R-phycoerythrin (Molecular Probes of Eugene, Oreg., USA) using the GENECHIP® Fluidics Station 450 and scanned with a Affymetrix GENECHIP® Scanner 3000 (Affymetrix of Santa Clara, Calif., USA) following the manufacturer's instructions. Fluorescent data were collected and converted to gene specific signal intensities using MicroArray Suite 5.0 (MAS5) software where mean fluorescence difference between perfect match and single mismatch probe sets containing gene-specific oligonucleotides are used to determine mRNA signal intensity. For analysis, mean mRNA signal intensity of replicate samples was determined for each of the experimental groups. Genes were initially filtered to remove those probes where either all samples were called Absent by the MAS5 software. Mean signal intensity values were subsequently compared between experimental groups to identify genes with average fold change typically greater than 2-fold.

A number of genes were differentially expressed in tumor-initiating cells, including the following genes, which showed elevated expression in $CD24^{-/low}CD44^+$ tumor-initiating cells: TGFβRIII, Unc5D, PNPLA4, KCNJ2, GABRB3, DPYD, SPAG1, ICK, STC2, DEFβ1, and predicted gene FLJ38736.

The gene expression profiles of the primary culture in growth and differentiation (see Example 3) were also compared to those of the H460T $CD24^{-/low}CD44^+$ and $CD24^{high}CD44^+$ populations. A significant fraction of the genes that were expressed at higher levels during differentiation of the primary culture were also expressed at higher levels in the $CD24^{high}CD44^+$ cells (FDR=0.0015). For statistical comparison of the H460T and 87426 data sets, the top 250 upregulated genes in the differentiated 87426 culture were compared in the H460T populations. FIG. 7D shows the expression difference for genes that are above noise level in the H460T data set. Statistical analysis yielded the False Discovery Rate of 0.0015. This analysis indicates that these very different experimental systems are physiological models of the differentiation hierarchy in NSCLC. The microarray data were confirmed by flow cytometry (FIGS. 7E-7F). Accordingly, additional markers for enrichment or isolation of tumor initiating cells, either by positive selection, by low level expression, or by depletion of differentiated cells, include those set forth in Tables 1 and 2 (see Example 3).

Example 6

Sox2 Regulates Differentiation of Lung Cancer Tumor Initiating Cells

Gene expression profiling was performed on a panel of $CD24^{-/low}CD44^+$ clones to compare the clones that transitioned to $CD24^{high}$ with the clones that were stable (>99% $CD24^{-/low}$). $CD24^{-/low}CD44^+$ cells were sorted from each clone and RNA was extracted for microarray analysis as described in Example 5.

Gene expression profiles for stable $CD24^{-/low}CD44^+$ clones and transitioning $CD24^{-/low}CD44^+$ clones were similar overall, but mRNA levels of some genes correlated with the transition efficiency. For example, Sox2 mRNA levels were higher in the transitioning clones than in the stable clones (FIG. 9A). Sox2 is a transcription factor that is required for pluripotency and self-renewal in stem cells (Avilion et al., *Genes Dev.*, 2003, 17: 126-140: Boyer et al., *Cell.* 2005, 122: 947-956) and can contribute to the induction of pluripotency in differentiated cells (Takahashi & Yamanaka, *Cell*, 2006, 126: 663-676). In parental H460T cells, Sox2 was expressed in the $CD24^{-/low}CD44^+$ tumor-initiating cells but not in the $CD24^{high}CD44^+$ cells.

To test whether Sox2 could regulate the transition from $CD24^{-/low}$ to $CD24^{high}$ expression, exogenous Sox2 was introduced into stable $CD24^{-/low}CD44^+$ clones. Expression vectors EX-T2547-M46 (Sox-2) and EX-M0425-M46 (Sox-11) from GeneCopoeia (Germantown, Md., USA) were introduced into H460T clones with the Amaxa nucleofector solution V, program T-020 (2 μg DNA per $10^6$ cells). Stable clones were transfected with Sox2-Flag, Sox11-Flag, empty vector, or no DNA. Forty-eight hours after transfection, G418 was added to 400 μg/ml. Cells were incubated in G418 for six days and subsequently without G418. Immunoblot analysis was performed as described in Example 2, which confirmed expression of the indicated transgenes (FIG. 9B). After a 6-day selection in G418 and two additional weeks in culture, all three stable $CD24^{-/low}CD44^+$ clones exhibited large fractions of $CD24^{high}CD44^+$ cells after transfection with Sox2-Flag but not Sox11-Flag or empty vector (FIGS. 9C-9D). These data indicated that Sox2 was sufficient to drive the transition from $CD24^{-/low}$ to $CD24^{high}$, indicating a role in the differentiation of multipotent tumor-initiating cells.

Example 7

Inhibition of Tumor Cell Growth Using Anti-5T4 Antibody/Drug Conjugates

The $CD24^{-/low}CD44^+$ population was more sensitive to an anti-5T4 antibody-drug conjugate than the $CD24^{high}CD44^+$ population in an cell viability assay and a colony growth assay. For each assay, antibody-calicheamicin AcBut-linked (AcBut-AcBut-[4-(4-acetylphenoxy) butanoic acid]) conjugates were prepared as described (Hamann et al., *Bioconjug. Chem.*, 2002, 13: 47-58). The effect of anti-5T4 huH8 antibody-drug conjugate or anti-CD22 antibody-drug conjugate on sorted cells was assessed using a cellular viability indicator ((3-(4,5-dimethylthiazol-2-yl)-5(3-carboxymethoxyphenol)-2-(4-sulfophenyl)-2H-tetrazolium (MTS) (Promega of Madison, Wis., USA) to determine the number of surviving cells following exposure to the drug treatment. Cells were sorted 18 hours prior to start of assay. Cells were seeded in 96-well microtiter plates at a density of 10000 cells per well and exposed to various concentrations of the drug. Following determination of the number of viable cells surviving 96 hours of drug exposure, the $IC_{50}$ of each treatment was calculated based on the logistic regression parameters derived from the dose-response curves. $IC_{50}$ values were calculated by logistic non-linear regression and are reported as the calicheamicin dimethyl hydrazide (CalichDMH) concentration from each treatment group that causes 50% loss of cell viability. $CD24^{-/low}CD44^+$ cells were more than ten-fold more sensitive to the anti-5T4-calicheamicin conjugate (FIG. 10A). No difference between the two populations was observed when treated with anti-CD22-calicheamicin conjugate or calicheamicin alone (FIG. 10A).

To perform a colony formation assay, cells were seeded in 24 well plate at a density of 5,000 cells per well. Twenty-four hours after seeding the cells were exposed to various concentrations of (0.000097, 0.000390, 0.00156, 0.00625, 0.025, 0.1, 0.4 ng calicheamicin equivalents/ml) of anti-5T4 H8-AcBut conjugate, anti-CD22 AcBut conjugate, or calicheamicin alone. Seventy-two hours after the drug exposure, cells were trypsinized, counted and 200 cells were plated in 6 well plates. After 8 days, the colonies were fixed and stained with methylene blue. The number of colonies per well was counted using a Stereoscope. $CD24^{-/low}CD44^+$ cells were more than ten-fold more sensitive to the conjugate (FIG. 10B). No difference between the two populations was observed when treated with anti-CD22-calicheamicin conjugate or calicheamicin alone (FIG. 10B).

Figure 11:
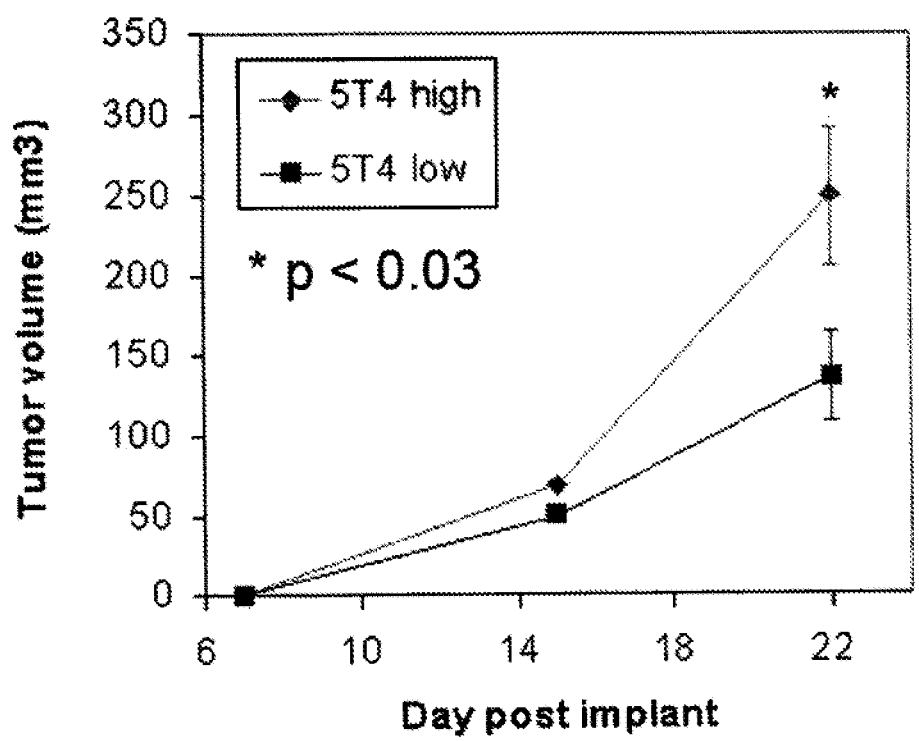
FIG. 11 is a line graph that shows tumor growth of 5T4$^{high}$ and 5T4$^{low}$ cells in H460T clonal line 24N-26, which showed higher expression than in the H460T parental cell line. Cells were sorted based upon 5T4 expression and implanted subcutaneously into mice. Values indicate the average tumor measurement ±SEM.

To test whether 5T4 expression was directly associated with tumorigenic potential, H460T cells were sorted based upon $5T4^{high}$ and $5T4^{low}$ expression and implanted subcutaneously into mice. Tumors from $5T4^{high}$ cells were larger than tumors from the $5T4^{low}$ cells (p<0.03; FIG. 11). For this experiment, H460T clonal line 24N-26 was used, which shows higher levels of 5T4 expression and increased resolution of $5T4^{high}$ and $5T4^{low}$ expression as compared to the parental line.

Example 8

Tumor Regression Using Anti-5T4 Antibody/Drug Conjugate

Nude (for 37622) or nod-scid (for 60274) mice were injected subcutaneously between the shoulder blades with fragments of low-passage primary implants. When the tumors reached the mass of 0.2 to 0.5 g, the tumors were staged to ensure uniformity of the tumor mass between various treatment groups prior to the administration of therapy. Anti-5T4 huH8 antibody and anti-CD33 p67.6 antibody were conjugated to calicheamicin via an amide linker as described (Hamann et al., *Bioconug. Chem.*, 2002, 13: 40-46). The "amide" linker restricts the release of calicheamicin to cells that internalize the antibody-drug conjugate (Hamann et al., *Bioconug. Chem.*, 2002, 13: 40-46). Antibody-drug conjugates or vehicle were each administered intraperitoneally in sterile saline (0.2 ml/mouse) on day 1 and the same treatment was repeated twice four days apart (Q4Dx3). The calicheamicin conjugates were administered at a dose of 160 µg/kg of CalichDMH. Tumors were measured at least once a week and their mass was as volume=$0.5\times$(tumor width$^2$)(tumor length). Mean tumor volume (±SEM) for each treatment group was calculated and compared to the vehicle-treated group for statistical significance using a one-sided t-test, with the error term for the t-test based on the pooled variance across all treatment groups. Tumor values for each treatment group were recorded up to 120 days after the initiation of treatment or until either tumor-bearing mice died or the tumors grew to 15% of the body weight at which time these mice were euthanized according to institutional regulations. The anti-CD33 conjugate served as control because these xenografts do not express CD33.

Figure 12A:
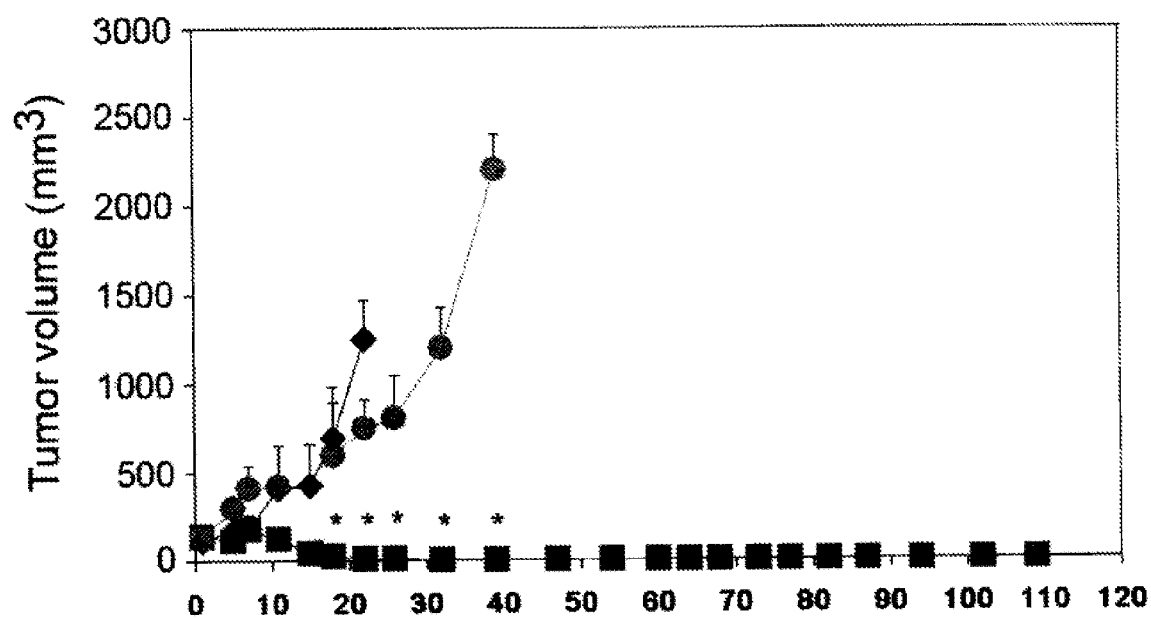
FIGS. 12A-12C show tumor volume regression of primary implant xenografts treated with an anti-5T4 antibody-calicheamicin conjugate. Diamond, vehicle; square, anti-5T4-calicheamicin conjugate; circle, anti-CD33-calicheamicin conjugate; triangle, cisplatin; asterisk (*), p<0.05.
Figure 12B:
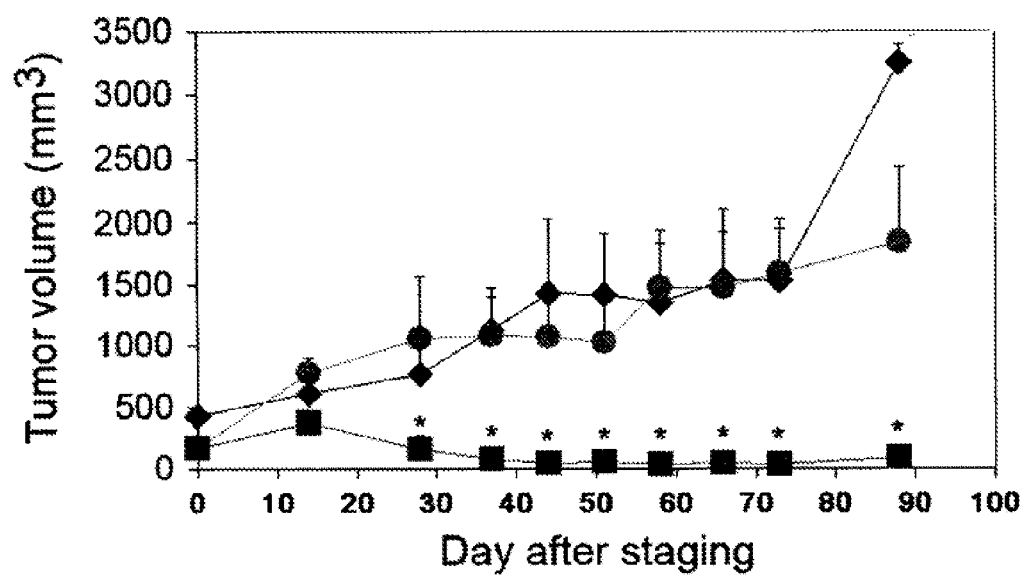
Figure 12C:
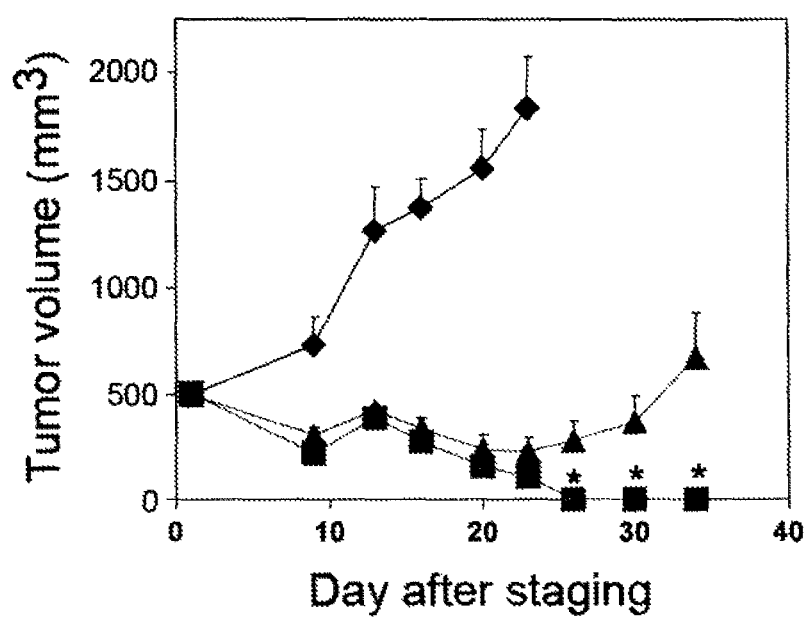
Figure 13:
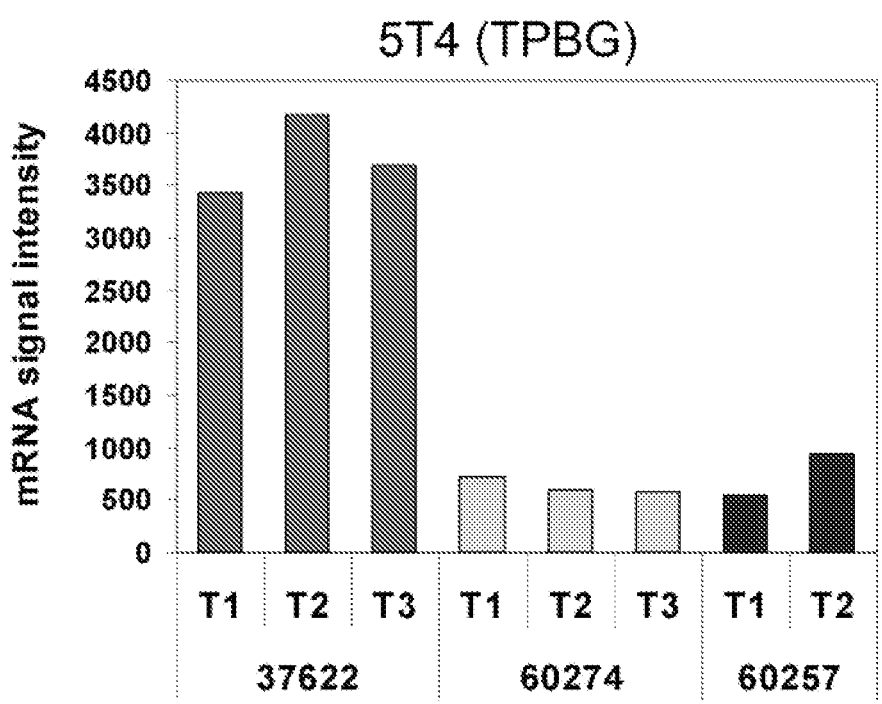
FIG. 13 is a bar graph showing 5T4 (TPBG) mRNA levels on an Affymetrix GENECHIP® oligonucleotide arrays hybridized with transcripts from multiple tumors (T1, T2, T3) of NSCLC primary implant lines 37622, 60274, and 60257. The 37622 xenografts were from nude mice and the 60274 and 60257 xenografts were from nod-scid mice.

Treatment with anti-5T4-calicheamicin conjugate completely eradicated the 37622 xenografts, and no regrowth was observed through the end of the study, 120 days after the last dose (FIG. 12A). Xenografts treated with vehicle or anti-CD33-calicheamicin conjugate grew into large tumors. Similarly, treatment of 60274 xenografts with the anti-5T4-calicheamicin conjugate regressed the tumors significantly (FIG. 12B). In contrast, treatment of 60274 tumors with cisplatin at the maximum tolerable dose reduced tumor size transiently, and the tumors quickly regrew after completion of the dosing regimen (FIG. 12C). 60274 cells express 5T4 at lower levels when compared to 37622 cells (FIG. 13). These results demonstrated a specific effect of an anti-5T4 antibody-calicheamicin conjugate on growth inhibition of NSCLC primary implants with heterogeneous 5T4 expression.

LENGTHY TABLES

The patent contains a lengthy table section. A copy of the table is available in electronic form from the USPTO web site (http://seqdata.uspto.gov/?pageRequest=docDetail&DocID=US09340774B2). An electronic copy of the table will also be available from the USPTO upon request and payment of the fee set forth in 37 CFR 1.19(b)(3).

What is claimed:

1. A method of testing efficacy of a cancer drug comprising:
   (a) providing an isolated tumor-initiating cell population comprising majority of cells expressing 5T4 oncofetal antigen at a level that is at least 2-fold higher than non-tumorigenic cells of the same origin;
   (b) contacting the tumor-initiating cell population with a cancer drug; and
   (c) measuring a change in tumorigenic potential of the tumor-initiating cell population following contacting the tumor-initiating cell population with the cancer drug.

2. The method of claim 1, wherein the isolated tumor-initiating cell population comprises at least 90% tumor-initiating cells, wherein the tumor-initiating cells (i) express 5T4 oncofetal antigen at a level that is at least 2-fold higher than non-tumorigenic cells of the same origin, (ii) are tumorigenic, (iii) are capable of migration, (iv) are capable of self-renewal, and (v) generate tumors comprising non-tumorigenic cells.

3. The method of claim 1, wherein the isolated tumor-initiating cell population comprises at least 95% tumor-initiating cells.

4. The method of claim 1, wherein the isolated tumor-initiating cell population expresses 5T4 oncofetal antigen at a level that is at least 5-fold higher than non-tumorigenic cells of the same origin.

5. The method of claim 4, wherein the isolated tumor-initiating cell population expresses 5T4 oncofetal antigen at a level that is at least 10-fold higher than non-tumorigenic cells of the same origin.

6. The method of claim 5, wherein the isolated tumor-initiating cell population expresses 5T4 oncofetal antigen at a level that is at least 20-fold higher than non-tumorigenic cells of the same origin.

7. The method of claim 1, wherein the isolated tumor-initiating cell population, which further expresses CD24 at a level that is at least 5-fold lower than non-tumorigenic cells of the same origin.

8. The method of claim 1, wherein the isolated tumor-initiating cell population further expresses CD44.

9. The method of claim 7, wherein the isolated tumor-initiating cell population further expresses CD44.

10. The method of claim 1, wherein the isolated tumor-initiating cell population is derived from a lung tumor.

11. The method of claim 1, wherein the isolated tumor-initiating cell population comprises one to ten cells and has the capacity to form a palpable tumor.

* * * * *